US005783556A

United States Patent [19]
Clark et al.

[11] Patent Number: 5,783,556
[45] Date of Patent: Jul. 21, 1998

[54] FORMULATED INSULIN-CONTAINING COMPOSITION

[75] Inventors: Ross G. Clark, Pacific; James Q. Oeswein, Moss Beach; Douglas A. Yeung, Fremont, all of Calif.

[73] Assignee: Genentech, Inc., South San Francisco, Calif.

[21] Appl. No.: 696,314

[22] Filed: Aug. 13, 1996

[51] Int. Cl.$^6$ .................... A61K 38/00; A61K 38/24; A61K 38/30
[52] U.S. Cl. .................... 514/4; 514/12; 514/21
[58] Field of Search .................... 514/4, 12, 21

[56] References Cited

U.S. PATENT DOCUMENTS 4,988,675  1/1991  Froesch et al. .................... 514/4

FOREIGN PATENT DOCUMENTS

| A-57908/90 | 1/1991 | Australia . |
|---|---|---|
| 123228 | 10/1984 | European Pat. Off. . |
| 128733 | 12/1984 | European Pat. Off. . |
| 440989 | 8/1991 | European Pat. Off. . |
| 561330 A1 | 9/1993 | European Pat. Off. . |
| 5043453 | 2/1993 | Japan . |
| WO 91/03253 | 3/1991 | WIPO . |
| WO 91/18621 | 12/1991 | WIPO . |
| WO 92/20367 | 11/1992 | WIPO . |
| WO 93/00110 | 1/1993 | WIPO . |
| WO 93/04691 | 3/1993 | WIPO . |
| WO 93/10806 | 6/1993 | WIPO . |
| WO 93/23071 | 11/1993 | WIPO . |
| WO 94/00010 | 1/1994 | WIPO . |
| WO 94/04030 | 3/1994 | WIPO . |
| WO 94/16722 | 8/1994 | WIPO . |
| WO 94/16723 | 8/1994 | WIPO . |
| 9534318 | 12/1995 | WIPO . |
| WO 95/34318 | 12/1995 | WIPO . |
| 9601125 | 1/1996 | WIPO . |
| 9602270 | 1/1996 | WIPO . |
| WO 96/01124 | 1/1996 | WIPO . |
| WO 96/01125 | 1/1996 | WIPO . |
| WO 96/02270 | 2/1996 | WIPO . |

OTHER PUBLICATIONS

*The Merck Index*, Budavari, ed., 11th edition, Rahway, NJ:Merck & Co., Inc. p. 49 (1989).

Amiel et al., "Effect of Diabetes and its COntrol on Insulin-like Growth Factors in Young Subject with Type I Diabetes" *Diabetes* 33(12):1175–1179 (Dec. 1984).

Arias et al., "Suppression of the Dawn Phenomenon by Somatostatin" *Diabetologia* 27(2):252A (abstract only 1984).

Baxter, R.C., "The Somatomedins: Insulin–Like Growth Factors" *Advances in Clin Chem.* 25:49–115 (1986).

Binoux, M., "Donnees recentes sur les somatomedines" *Annales d'Endocrinologie* 41:157–191 (1980).

Blethen et al., "Effect of Pubertal Stage and Recent Blood Glucose Control on Plasma Somatomedin C in Children with Insulin–dependent Diabetes Mellitus" *Diabetes* 30:868–872 (1981).

Boulware et al., "Phosphate and Potassium Lowering Effects of Insulin–like Growth Factor–I in Humans: Comparison with Insulin" *The Endocrine Society*, San Antonio, (74th Annual Meeting) pp. 78:106 (abstract only) Jun. 1992).

Brismar et al., "Effect of Insulin on the Hepatic Production of Insulin–like Growth Factor–Binding Protein–1 (IGFBP–1), IGFBP–3, and IGF–I in Insulin–Dependent Diabetes" *J. Clin. Endocrinol. Metab.* 79(3):872–878 (1994).

Campbell, "The Evolution of Insulin Therapy" *Pharmacy Times*, Romaine Pierson vol. 59:40–44 (Oct. 1993).

Campbell et al., "Pathogenesis of the Dawn Phenomenon in Patients with Insulin–Dependent Diabetes Mellitus" *New England J. of Medicine* 312(23):1473–1479 (1985).

Campbell et al., "Prevention of the Dawn Phenomenon (Early Morning Hyperglycemia) in Insulin–Dependent Diabetes Mellitus by Bedtime Intranasal Administration of a Long–Acting Somatostatin Analog" *Metabolism* 37(1):34–37 (1988).

Cheetham et al., "The Effects of Recombinant Human Insulin–like Growth Factor I on Growth Hormone Secretion in Adolescents With Insulin Dependent Diabetes Mellitus" *Clin. Endocrinol.* 40:515–522 (1994).

Cheetham et al., "The Effects of Recombinant Insulin–like Growth Factor I Administration on Growth Hormone Levels and Insulin Requirements in Adolescents With Type I (Insulin–dependent) Diabetes Mellitus" *Diabetologia* 36:678–681 (1993).

Clemmons and Van Wyk, "Somatomedin: physiological control and effects on cell proliferation" *Handbook Exp. Pharmacol.* 57:161–208 (1981).

Davidson et al., "Suppression of Sleep–Induced Growth Hormone Secretion by Anticholinergic Agent Abolishes Dawn Phenomenom" *Diabetes* 37:166–171 (1988).

(List continued on next page.)

*Primary Examiner*—Cecilia J. Tsang
*Assistant Examiner*—P. Lynn Touzeau
*Attorney, Agent, or Firm*—Janet E. Hasak

[57] ABSTRACT

Formulations containing NPH insulin are useful for treating hyperglycemic disorders, such as diabetes, in a mammal in need of treatment. One such formulation, which is preferably administered parenterally, more preferably by injection, comprises IGF-I and NPH insulin, in amounts of from or about 1 to 10 mg IGF-I and from or about 0.2 to 2 mg NPH insulin in a pharmaceutically acceptable carrier. Another such formulation comprises IGF-I and NPH insulin in an acetic acid salt buffer. Still another formulation comprises IGF-I and NPH insulin in a weight ratio of NPH insulin to IGF-I of from or about 10:1 to 1:50 (w/w), from or about 0.05 to 0.3M of an osmolyte, from or about 0.1 to 10 mg/mL of a stabilizer, and from or about 5 to 100 mM of a buffer at from or about pH 5 to 7. A still further composition comprises NPH insulin in an acetic acid salt buffer.

48 Claims, 22 Drawing Sheets

OTHER PUBLICATIONS

De Feo et al., "A Growth Hormone–induced Hepatic Insulin Resistance, Not an Increase in Plasma Insulin Clearance, is the Cause of the Dawn Phenomenom in Type I (insulin–dependent) Diabetes" *Diabetologia* (abstract only) 29:532A (1986).

Diabetes Control and Complications Trial Research, "The Effect of Intensive Treatment of Diabetes on the Development and Progression of Long–term Complications in Insulin–dependent Diabetes Mellitus" *New England J. of Medicine* 329(14):977–986 (1993).

Dunger et al., "Insulin–like Growth Factors (IGFs) and IGF–I Treatment in the Adolescent With Insulin–dependent Diabetes Mellitus" *Metabolism* 44(10):119–123 (Suppl. 4 1995).

Edge et al., "Increased Overnight Growth Hormone Concentrations in Diabetic Compared With Normal Adolescents" *J. Clin. Endocrinol Metab.* 71(5):1356–1362 (1990).

Eizirik et al., "Insulin–Like Growth Factor I Does not Inhibit Insulin Secretion in Adult Human Pancreatic Islets in Tissue Culture" *European J. of Endocrinology* 133(2):248–250 (1995).

Elahi et al., "Hemodynamic and metabolilc responses to human insulin–like growth factor I (IGF–I) in men" *Modrn Concepts of Insulin–Like Growth Factors*, Spencer, EM. ed., New York:Elsevier Science Publ. Co. pp. 219–224 (1991).

Froesch et al., "Metabolic and Therapeutic Effects of Insulin–Like Growth Factor I" *Horm. Res.* 42:66–71 (1994).

Fuller et al., "Stimulation of Cardiac Protein Synthesis by Insulin–like Growth Factors" *Biochemical Society Transactions* 19:277S (1991).

Furnsinn et al., "Insulin–Like Growth Factor–I Inhibits Insulin and Amylin Secretion in Conscious Rats" *Endocrinology* 135(5):2144–2149 (1994).

Guler et al., "Effects of Insulin–like Growth Factor I in Man" *Acta Paediatr. Scand.* 367:52–54 (Suppl. 1990).

Guler et al., "Short–term metabolic effects of recombinant human insulin–like growth factor I in healthy adults" *New England J. of Medicine* 317(3):137–140 (1987).

Gunn, et al., "Anabolic Steroids do not Alter the Effect of Insulin and IGF–2 on Protein Breakdown in L6 Muscle Cells" *Biochem. Arch.* 5:53–59 (1989).

Hall et al., "Serum Levels of Insulin–like Growth Factor (IGF) I, II and IGF Binding Protein in Diabetic Adolescents Treated With Continuos Subcutaneous Insulin Infusion" *J. Inter. Med.* 225:273–278 (1989).

Hermansen et al., "Diurnal Plasma Profiles of Metabolite and Hormone Concentration in Insulin–dependent Diabetic Patients During Conventional Insulin Treatment and Continuous Subcutaneous Insulin Infusion" *Acta Endocrinol. (Copenh)* 114:433–439 (1987).

Jabri et al., "Adverse effects of recombinant human insulin–like growth factor I in obese insulin–resistant type II diabetic patients" *Diabetes* 43:369–374 (1994).

Jacob et al., "Metabolic Effects of IGF–I and Insulin in Spontaneouosly Diabetic BB/w Rats" *Am. J. Physiol.* 206:E262–E268 (1991).

Johansen et al., "Diurnal Serum Growth Hormone Levels in Poorly and Well–controlled Juvenile Diabetics" *Diabetes* 20:239–245 (Apr. 1971).

Kerr et al., "Effect of Insulin–like Growth Factor I on the Responses to and Recognition of Hypoglycemia" *American Diabetes Association (ADA), San Antonio, Texas, Jun. 20–23, 1992* (abstract), 52nd Annual Meeting edition.

Kerr et al., "Effect of Insulin–like Growth Factor–1 on the Responses to and Recognition of Hypoglycemia in Humans" *J. Clin. Invest.* 91:141–147 (1993).

Kissel et al., "Applikatiosformen des Insulins (Forms of Administration of Insulin—English translation provided)" *Deutsche Apotheker–Zeitung (Germany)* 134(7):25–39 (1994).

Kuzuya et al., "Trial of insulinlike growth factor I therapy for patients with extreme insulin resistance syndromes" *Diabetes* 42:696–705 (1993).

Lanes et al., "Impaired Somatomedin Generation Test in Children With Insulin–dependent Diabetes Mellitus" *Diabetes* 34:156–160 (1985).

Leahy et al., "Insulin–Like Growth Factor–I at Physiological Concentrations is a Potent Inhibitor of Insulin Secretion" *Endocrinology* 126(3):1593–1598 (1990).

Lewitt et al., "Insulin–like Growth Factor–binding Protein–1 Modulates Blood Glucose Levels" *Endocrinology* 129(4):2254–2265 (1991).

Lieberman et al., "Effects of recombinant human insulin–like growth factor–I (rhIGF–I) on total and free IGF–I concentrations, IGF–binding proteins, and glycemic response in humans" *J. Clin. Endocrinol. and Metab.* 75(1):30–36 (1992).

Mathe, "Relations of Hormones and Growth Factors at the Crossroad of Pathogenesis and Pharmacotherapeutics. The Case of Diabetes Mellitus" *Biomedicine and Pharmacotherapy* 49/5:221–224 (1995).

Molnar et al., "Diurnal Growth Hormone and Glucose Abnormalities in Unstable Diabetics: Studies of Ambulatory–fed Subjects During Continuous Blood Glucose Analysis" *J. Clin. Endocrin. Metab.* 34(5):837–846 (1972).

Morrow et al., "Recombinant Human (rh) IGF–1 Reverses Hyperglycemia and Improves Insulin Sensuitivity in Severe Insulin Resistance" *Diabetes–53rd Annual Meeting, Jun. 12–15, 1993* (abstract No. 269) 42:83A (Suppl. 1 1993).

Nieves–Rivera et al., "Alterations in Growth Hormone Secretion and Clearance in Adolescent Boys with Insulin–Dependent Diabetes Mellitus" *J. Clin. Endo. Metab.* 77(3):638–643 (1993).

Press et al., "Importance of Raised Growth Hormone Levels in Mediating the Metabolic Derangements of Diabetes" *New England J. of Medicine* 310:810–815 (1984).

Quin et al., "Acute Response to Recombinant Insulin–like Growth Factor I in a Patient with Mendenhall's Syndrome" *New England J. of Medicine* 323:1425–1426 (1990).

Randazzo et al., "Characterization of the Growth of Murine Fibroblasts That Express Human Insulin Receptors" *Exp. Cell Res.* 190(1):31–39 (1990).

Rinderknecht and Humbel, "The amino acid sequence of human insulin–like growth factor I and its structural homology with proinsulin" *Journal of Biological Chemistry* 253(8):2769–2776 (1978).

Rinderknecht and Humbel, "Polypeptides with nonsuppressible insulin–like and cell–growth promoting activities in human serum: isolation, chemical characterization, and some biological properties of forms I and II" *Proc. Natl. Acad. Sci. USA* 73(7):2365–2369 (1976).

Ross et al., "The Role of Insulin, Growth Hormone and IGF–I as Anabolic Agents in the Critically Ill" *Intensive Care Med.* 19(2):S54–57 (Suppl. 1993).

Saad et al., "Low–doses of Inulin–like Growth Factor–I Improve Insulin Sensitivity" *Diabetologia* (Abstract) 37:A40 (Supp. 1 1994).

Schalch et al., "Short-Term Effects of Recombinant Human Insulin-Like Growth Factor I on Metabolic Control of Patients with Type II Diabetes Mellitus" *J. of Clinical Endocrinology & Metabolism* 77(6):1563–1568 (1993).

Schalch et al., "Short-term metabolic effects of recombinant human insulin-like growth factor I (rhIGF-I) in type II diabetes mellitus" *Modern Concepts of Insulin-Like Growth Factors*, Spencer, ed., New York:Elsevier Science Publ. Co. pp. 705–713 (1991).

Schoenle et al., "Recombinant human insulin-like growth factor I(rhIGF I) reduces hyperglycaemia in patients with extreme insulin resistance" *Diabetologia* 34:675–679 (1991).

Sherwin et al., "Metabolic Effects of Insulin–like Growth Factor I in Normal Humans" *Horm. Res.* 41:97–101 (Suppl. 2 1994).

Shishko et al., "Insulin–like Growth factors and Binding Proteins in Patients With Recent–onset Type I (insulin–dependent) Diabetes Mellitus: Influence of Diabetes Control and Intraportal Insulin Infusion" *Diabetes Research and Clin. Prac.* 25:1–12 (1994).

Shojaee-Moradie et al., "A Comparison of the Effects of Insulin–like Growth Factor–I, Insulin and Combined Infusions of Insulin and Insulin-like Growth Factor–I on Glucose Metabolism in Dogs" *European Journal of Clinical Investigation (United Kingdom)* 25(12):920–928 (1995).

Sieradzki et al., "Stimulatory Effect of Insulin–Like Growth Factor–I on [3H] thymidine Incorporation, DNA Content and Insulin Biosynthesis and Secretion of Isolated Pancreatic Rat Islets" *J. of Endocrinology* 117(1):59–62 (1988).

Sonksen et al., "Growth Hormone and Diabetes Mellitus" *Horm. Res.* 40:68–79 (1993).

Sperling et al., "Daily Production and Metabolic Clearance of Growth Hormone in Juvenile Diabetes Mellitus" *Diabetologia* 9:380–383 (1973).

Takano et al., "Effects of sc Administration of Recombinant Human Insulin–like Growth Factor I (IGF–I) on Normal Human Subjects" *Endocrinol. Japan* 37(2):309–317 (1990).

Tanner et al., "Comparative rapidity of response of height, limb muscle and limb fat to treatment with human growth hormone in patients with and without growth hormone deficiency" *Acta Endocrinologica* 84:681–696 (1977).

Tomas et al., "Cojoint IGF–I and Insulin Shows Diverse Interactive Effects in Diabetic Rats" *Diabetes* 45:170–177 (1996).

Umpleby et al., "Effects of Insulin–like Growth Factor–I (IGF–I), Insulin and Combined IGF–I–insulin Infusions on Protein Metabolism in Dogs" *Eur. J. Clin. Invest.* 24:337–334 (1994).

Underwood et al., "Regulation of somatomedin–c/insulin––like growth factor I by nutrients" *Hormone Res.* 24:166–176 (1986).

Usala et al., "Brief report: treatment of insulin–resistant diabetic ketoacidosis with insulin–like growth factor I in an adolescent with insulin–dependent diabetes" *New England J. of Medicine* 327(12):853–857 (1992).

Uthne et al., "Effects of human somatomedin preparations on membrane transport and protein synthesis in the isolated rat diaphram" *J. Clin. Endocrinol. Metab.* 39(3):548–554 (1974).

Van Schravendijk et al., "Direct Effect of Insulin and Insulin–Like Growth Factor–I on the Secretory Activity of Rat Pancreatic Beta Cells" *Diabetologia* 33(11):649–653 (1990).

Van Wyk et al., "The somatomedins: a family of insulinlike hormones under growth hormone control" *Recent Prog. Horm. Res.* 30:259–318 (1974).

Vlachopapadopoulou et al., "Metabolic and Clinical Response to Recombinant Human Insulin–like Growth Factor I in Myotonic Dystrophy—A Clinical Research Center Study" *J. Clin. Endo. Metab.* 80(12):3715–3723 (1995).

Wilson, "Growth Abnormalities in Diabetes Mellitus" *Contemporary Issues in Endocrinology and Metabolism*, R. L. Hintz and R. G. Rosenfeld, ed. vol. 4:59–80 (1987).

Wilton et al., "Treatment with recombinant human insulin––like growth factor I of children with growth hormone receptor deficiency (Laron syndrome)" *Acta Paediatr Suppl* 383:137–141 (1992).

Winter et al., "Somatomedin Activity and Diabetic Control in Children With Insulin–dependent Diabetes" *Diabetes* 28:952–954 (1979).

Winter et al., "Somatomedin Activity in the Mauriac Syndrome" *J. Pediatr.* 97(4):598–600 (1980).

Zenobi et al., "Effects of insulin–like growth factor–I on glucose tolerance, insulin levels, and insulin secretion" *J. Clin. Invest.* 89:1908–1913 (1992).

Zenobi et al., "Insulin–like growth factor–I improves glucose lipid metabolism in type 2 diabetes mellitus" *J. Clin. Invest.* 90:2234–2241 (1992).

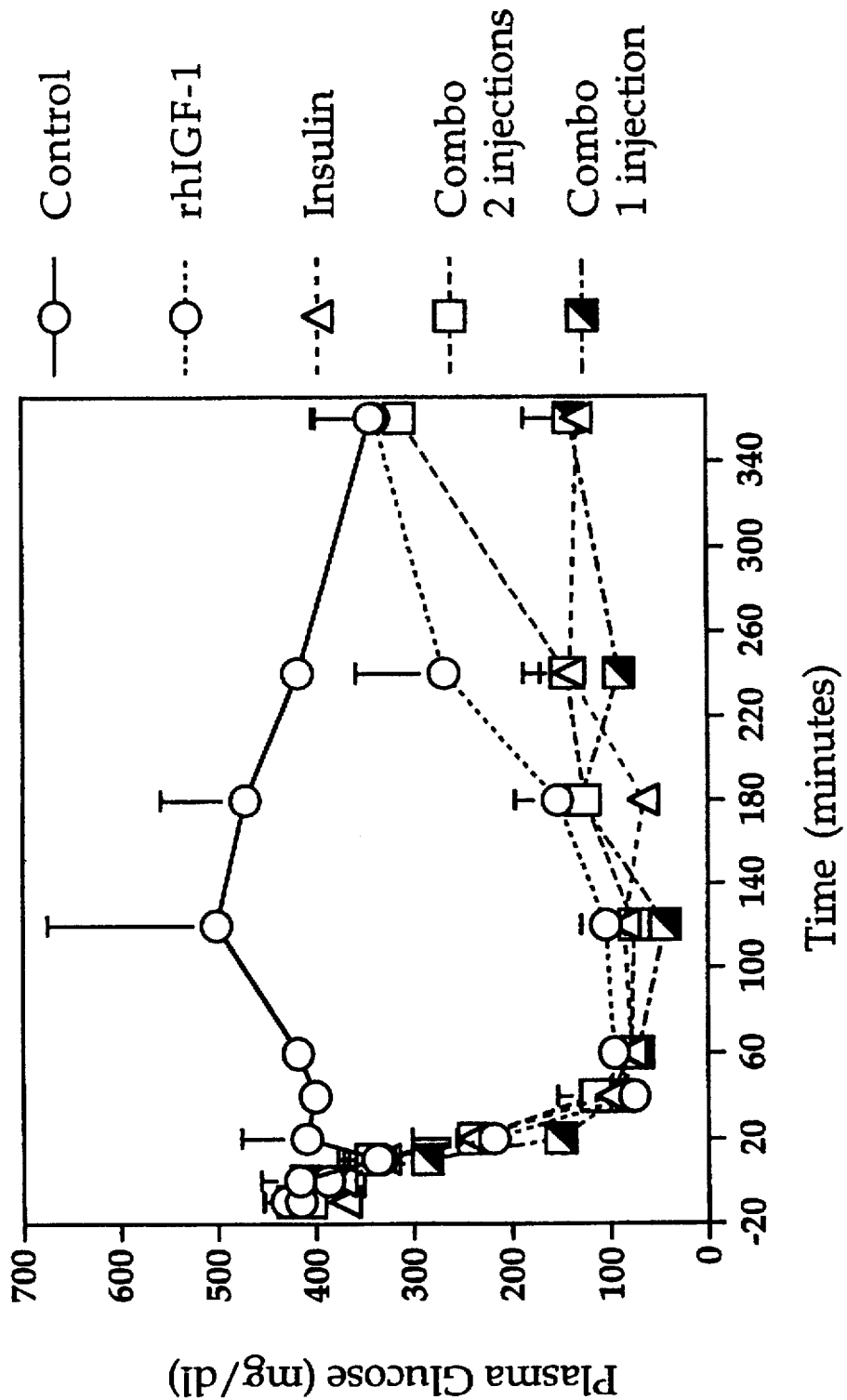

FORMULATED INSULIN-CONTAINING COMPOSITION

BACKGROUND OF THE INVENTION

1. Field of the Invention

This invention relates to formulations containing insulin-like growth factor-I (IGF-I) and insulin useful, for example, in a method of treating hyperglycemic disorders such as diabetes in patients.

2. Description of Related Art

There is a clear need to improve the treatment of diabetes. One improvement is to use IGF-I as a therapeutic agent for this purpose. Human IGF-I is a 7649-dalton polypeptide with a pI of 8.4 (Rinderknecht and Humbel, *Proc. Natl. Acad. Sci. USA*, 73: 2365 (1976); Rinderknecht and Humbel, *J. Biol. Chem.*, 253: 2769 (1978) belonging to a family of somatomedins with insulin-like and mitogenic biological activities that modulate the action of growth hormone (GH). Van Wyk et al., *Recent Prog. Horm. Res.*, 30: 259 (1974); Binoux, *Ann. Endocrinol.*, 41: 157 (1980); Clemmons and Van Wyk. *Handbook Exp. Pharmacol.*, 57: 161 (1981); Baxter, *Adv. Clin. Chem.*, 25: 49 (1986); U.S. Pat. No. 4,988,675; WO 91/03253; and WO 93/23071. IGF-I naturally occurs in human body fluids, for example, blood and human cerebral spinal fluid. Most tissues and especially the liver produce IGF-I together with specific IGF-binding proteins. Like GH, IGF-I is a potent anabolic protein. See Tanner et al., *Acta Endocrinol.*, 84: 681–696 (1977); Uthne et al., *J. Clin. Endocrinol. Metab.*, 39: 548–554 (1974). See also Ross et al., *Intensive Care Med.*, 19 Suppl. 2: S54–57 (1993), which is a review of the role of insulin, growth hormone, and IGF-I as anabolic agents in the critically ill.

Unlike most other growth factors, the IGF's are present in high concentrations in the circulation, but only a small fraction of IGF is not protein bound. The overwhelming majority of IGF circulates as part of a non-covalently associated ternary complex composed of IGF-I or IGF-II, insulin-like growth factor binding protein-3 (IGFBP-3), and a large protein termed the acid-labile subunit (ALS). This complex is composed of equimolar amounts of each of the three components. The ternary complex of IGF plus IGFBP-3 plus ALS has a molecular weight of approximately 150,000 daltons, and it has been suggested that the function of this complex in the circulation may be to serve as a reservoir and buffer for IGF-I and IGF-II preventing rapid changes of free IGF-I. Although IGF-I is produced in many tissues, most circulating IGF-I is believed to be synthesized in the liver.

IGF-I may be purified from natural sources, e.g., human serum (Rinderknecht and Humbel, *J. Biol. Chem.*, supra), or made recombinantly (e.g., EP 123,228 and 128,733). Various methods for formulating IGF-I have been described. These include, for example, EP 440,989, which discloses a method for preparing a dried composition of IGF-I, which comprises drying a solution containing IGF-I together with a strong acid, WO 91/18621 on formulating IGF-I in a citrate buffer at pH 6, U.S. Pat. No. 5,374,620 on formulating IGF-I and GH in a growth-promoting composition, copending U.S. Ser. No. 08/071,819 filed Jun. 4, 1993 on formulating IGF-I in an acetate buffer, PCT/SE94/00010 on a stable solution containing IGF-I in a phosphate buffer in an amount of 50 mmol or less, giving pH of 5.5 to 6.5, which is isotonic and suitable for injection, and Wo 95/34318 on a solution comprising IGF-I in an aqueous solution with a reduced concentration of oxygen.

IGF-I has hypoglycemic effects in humans similar to insulin when administered by intravenous bolus injection, but also promotes positive nitrogen balance. Underwood et al., *Hormone Research*, 24: 166 (1986). IGF-I is known to exert glucose-lowering effects in both normal (Guler et al., *N. Engl. J. Med.*, 317: 137–140 [1987]) and diabetic individuals (Schoenle et al., *Diabetologia*, 34: 675–679 [1991]; Zenobi et al., *J. Clin. Invest.*, 90: 2234–2241 [1992]) [see also Sherwin et al., *Hormone Research*, 41 (Suppl. 2): 97–101 (1994); Takano et al., *Endocrinol. Japan*, 37: 309–317 (1990); Guler et al., *Acta Paediatr. Scand. (Suppl.)*, 367: 52–54 (1990)], with a time course described as resembling regular insulin. See also Kerr et al., "Effect of Insulin-like Growth Factor 1 on the responses to and recognition of hypoglycemia," American Diabetes Association (ADA), 52nd Annual Meeting, San Antonio, Tex., Jun. 20–23, 1992, which reported an increased hypoglycemia awareness following rhIGF-I administration. In addition, single administration of rhIGF-I reduces overnight GH levels and insulin requirements in adolescents with IDDM. Cheetham et al., *Clin. Endocrinol.*, 40: 515–555 (1994); Cheetham et al., *Diabetologia*, 36: 678–681 (1993).

Recombinant human IGF-I administered to Type II diabetics as reported by Schalch et al., *J. Clin. Metab.*, 77: 1563–1568 (1993) demonstrated a fall in both serum insulin as well as a paralleled decrease in C peptide levels which indicated a reduction in pancreatic insulin secretion after five days of IGF-I treatment. This effect has been independently confirmed by Froesch et al., *Horm. Res.*, 42: 66–71 (1994). In vivo studies in normal rats also illustrate that IGF-I infusion inhibits pancreatic insulin release. Fursinn et al., *Endocrinology*, 135: 2144–2149 (1994). In addition, in pancreas perfusion preparations IGF-I also suppresses insulin secretion. Leahy et al., *Endocrinology*, 126: 1593–1598 (1990). Despite these clear in vivo inhibitory effects of IGF-I on insulin secretion in humans and animals, in vitro studies have not yielded such uniform results.

In vitro studies using multiple concentrations of both IGF-I and glucose have shown various degrees of inhibition of insulin secretion, e.g., from no effect (Sreradzeri et al., *J. Endocrinol.*, 117: 59–62 [1988]) to a 30% decrease in insulin release utilizing physiological levels of IGF-I. Van Schravendijk et al., *Diabetologia*, 33: 649–653 (1990). In a recent study using human pancreatic islets, Eizirik et al., *Eur. J. Endocr.*, 133: 248–250 (1995) found no effect of IGF-I on medium insulin accumulation or on glucose-stimulated insulin release. The investigators speculate that the effect of IGF-I seen in vivo on insulin secretion may be secondary to the extra-pancreatic effects of IGF-I rather than its direct effects on the pancreas. Therefore, the mode and site of action of IGF-I on insulin secretion are not fully understood.

A number of biochemical changes induced by short-term rhIGF-I administration are described in the literature. Prominent among these is a phosphate and potassium lowering effect of recombinant human IGF-I (rhIGF-I) reported in healthy subjects during euglycemic clamp. Boulware et al., "Phosphate and potassium lowering effects of insulin-like growth factor I in humans: comparison with insulin" The Endocrine Society, 74th Annual Meeting, San Antonio, Tex., 1992, Jun. 24–27. See also Guler et al., *Acta Paediatr. Scand. (Suppl.)*, 367, supra.

Type I or insulin-dependent diabetes mellitus (IDDM) is associated with abnormalities of insulin and IGF's. To date, insulin "replacement" therapy through peripheral insulin administration has been the mainstay of therapy in IDDM for over 70 years. However, results from numerous trials, including the Diabetes Control and Complications Trial, have now clearly demonstrated that peripheral insulin administration alone is inadequate for normalizing glucose homeostasis. DCCT Research Group, *N. Eng. J. Med.*, 329: 977–986 (1993).

Numerous studies have demonstrated an association between IDDM and specific biochemical derangements of the GH-IGF axis. Winter et al., *J. Pediatr.*, 97: 598–600 (1980); Wilson, "Growth Abnormalities in Diabetes Mellitus", in: *Contemporary Issues in Endocrinology and Metabolism*, R. L. Hintz and R. G. Rosenfeld, ed., Volume 4 (1987), pp. 59–79. These abnormalities are particularly striking when IDDM is poorly controlled and include the presence of elevated plasma levels of GH, low plasma levels of IGF-I, normal to low levels of IGFBP-3, and high levels of IGFBP-1. Nieves-Rivera et al., *J. Clin. Endo. Metab.*, 7.7: 638–643 (1993); Hermansen et al., *Acta Endocrinol. (Copenh)*, 114: 433–439 (1987); Amiel et al., *Diabetes*, 33: 1175–1179 (1984); Blethen et al., *Diabetes*, 30: 868–872 (1981); Sperling et al., *Diabetologia*, 9: 380–383 (1973); Edge et al., *J. Clin. Endocrin. Metab.*, 71: 1356–1361 (1990); Molnar et al., *J. Clin. Endocrin. Metab.*, 34: 837–846 (1972); Johansen and Hansen, *Diabetes*, 20: 239–245 (1971); Shishko et al., *Diabetes Research and Clin. Prac.*, 25: 1–12 (1994); Brismar et al., *J. Clin. Endocrin. Metab.*, 79: 872–878 (1994). The likely cause of these derangements appears to be sub-physiologic insulin delivery to the liver, the primary source of circulating IGF-I, IGFBP-3, ALS, and IGFBP-1. Winter et al., *Diabetes*, 28: 952–954 (1979); Hall et al., *J. Inter. Med.*, 225: 273–278 (1989).

Most actions of GH are mediated by IGF-I, and the negative IGF-I feedback to the hypothalamic-pituitary unit is a key regulator of GH secretion. The reduced IGF-I feedback in IDDM results in a compensatory increase in pituitary release of GH. Hall et al., supra; Lanes et al., *Diabetes*, 34: 156–160 (1985). There is substantial evidence that this secondary elevation of GH has deleterious consequences in patients with IDDM. For example, high GH levels during sleep contribute to the increase in nocturnal insulin requirements and early morning fasting hyperglycemia. Press et al., *N. Eng. J. Med.*, 310: 810–815 (1984); Defeo et al., *Diabetologia*, 29: 532A (1986); Campbell et al., *N. Eng. J. Med.*, 312: 1473–1479 (1985); Campbell et al., *Metabolism*, 37: 34–37 (1988); Arias et al., *Diabetologia*, 27: 252A (1984); Davidson et al., *Diabetes*, 37: 166–171 (1988). In addition, the elevated GH levels have been implicated as directly contributing to the microvascular complications of IDDM. Sonksen et al., *Horm. Res.*, 40: 68–79 (1993).

RhIGF-I has the ability to improve insulin sensitivity. For example, rhIGF-I (70 µg/kg bid) improved insulin sensitivity in non-diabetic, insulin-resistant patients with myotonic dystrophy. Vlachopapadopoulou et al., *J. Clin. Endo. Metab.*, 12: 3715–3723 (1995). Saad et al., *Diabetologia* 37: Abstract 40 (1994) reported dose-dependent improvements in insulin sensitivity in adults with obesity and impaired glucose tolerance following 15 days of rhIGF-I treatment (25 µg and 100 µg/kg bid). RhIGF-I also improved insulin sensitivity and glycemic control in some patients with severe type A insulin resistance (Schoenle et al., *Diabetologia* 34: 675–679 [1991]; Morrow et al., *Diabetes*, 42 (Suppl.): 269 [1993] (abstract); Kuzuya et al., *Diabetes*, 42: 696–705 [1993]) or others with non-insulin dependent diabetes mellitus. Schalch et al., "Short-term metabolic effects of recombinant human insulin-like growth factor I (rhIGF-I) in type II diabetes mellitus", in: Spencer E. M., ed., *Modern Concepts of Insulin-like Growth Factors* (New York: Elsevier: 1991) pp. 705–715; Zenobi et al., *J. Clin. Invest.*, 90: 2234–2241 (1993).

Though insulin resistance has not been considered a prominent feature of type I diabetes, it is clearly present in some individuals and may be most clinically important during adolescence. As GH has well known anti-insulin effects, the elevated GH levels during adolescence may mediate much of this insulin resistance. Press et al., supra; Defeo et al., supra; Campbell et al., *N. Eng. J. Med.*, supra. Campbell et al., *Metabolism*, supra; Arias et al., supra; Davidson et al., supra.

A general scheme for the etiology of some clinical phenotypes which give rise to insulin resistance and the possible effects of administration of IGF-I on selected representative subjects is given in several references. See, e.g., Elahi et al., "Hemodynamic and metabolic responses to human insulin-like growth factor-1 (IGF-I) in men," in: *Modern Concepts of Insulin-Like Growth Factors*, (Spencer, E. M., ed.), Elsevier, New York, pp. 219–224 (1991); Quinn et al., *New Engl. J. Med.*, 323: 1425–1426 (1990); Schalch et al., "Short-term metabolic effects of recombinant human insulin-like growth factor 1 (rhIGF-1) in type 11 diabetes mellitus", in: *Modern Concepts of Insulin-Like Growth Factors*, (Spencer, E. M., ed.), Elsevier, New York, pp. 705–714 (1991); Schoenle et al., *Diabetologia*, 34: 675–679 (1991); Usala et al., *N. Eng. J. Med.*, 327: 853–857 (1992); Lieberman et al., *J. Clin. Endo. Metab.*, 75: 30–36 (1992); Zenobi et al., *J. Clin. Invest.*, 90: 2234–2241 (1992); Zenobi et al., *J. Clin. Invest.*, 89: 1908–1913 (1992); Kerr et al., *J. Clin. Invest.*, 91: 141–147 (1993). WO 94/16722 discloses a method of chronic modification of cell barrier properties by exposing a cell to a modification-effective amount of IGF-I for at least about seven days and a method of chronic amelioration or reversal of insulin resistance. However, when IGF-I was used to treat type II diabetes patients in the clinic at a dose of 120–160 µg/kg twice daily, the side effects outweighed the benefit of the treatment. Jabri et al., *Diabetes*, 43: 369–374 (1994). See also Wilton, *Acta Paediatr.*, 383: 137–141 (1992) regarding side effects observed upon treatment of patients with IGF-I.

U.S. Pat. No. 4,988,675 describes treatment of type II diabetics with IGF-I. U.S. Pat. No. 5,466,670 describes treatment of type I diabetics with IGF-I, WO 91/03253 reports use of IGF-I to treat severe insulin-resistant diabetics, and WO 96/01124 describes use of IGF-I to prevent diabetes, delay clinical onset of diabetes, and provide a protective effect against diabetes.

The treatments of choice in type II diabetes have become combination therapies. These combinations historically involved the use of multiple forms of insulin, short-acting insulin, intermediate-acting, and long-acting insulins. Review articles on insulin formulations include Kissel and Volland, *Deutsche Apotheker-Zeitung*, 134: 25 (1994) and Campbell, *Pharmacy Times*, 59: 40 (1993). More recently, combinations of insulin with other anti-diabetic drugs, which are taken orally such as sulphonylureas and biguanides, have become commonplace.

As to combinations of IGF and insulin, Genn et al., *Biochem. Arch.*, 5: 53–59 (1989) discloses the anabolic effect of insulin and IGF-II. Jacob et al., *Am. J. Physiol.*, 260: E262–E268 (1991) discloses the metabolic effects of IGF-I and insulin in spontaneously diabetic BB/w rats; see also U.S. Pat. No. 4,876,242. Furthermore, the stimulation of cardiac protein synthesis after treatment with insulin and IGF is disclosed by Fuller et al., *Biochem. Soc. Trans.*, 19: 277S (1991). The experiments have been performed in vitro with freshly isolated cardiac myocytes. The effects on protein metabolism after treatment with insulin and IGF of dogs which have been starved overnight are reported by Umpleby et al., *Eur. J. Clin. Invest.*, 24: 337–344 (1994). Shojaee-Moradie et al. discloses a comparison of the effects of IGF-I, insulin, and combined infusions thereof on glucose metabolism in dogs. Randazzo and Jarett, *Exp. Cell Res.*, 190 (1): 31–39 (1990) discloses characterization of the growth of murine fibroblasts that express human insulin receptors and the effect of IGF-I and insulin on DNA synthesis thereof. Tomas et al., *Diabetes*, 45: 170–177 (1996) discloses the effects of joint IGF-I and insulin infusion on diabetic rats. Dunger et al., *Metabolism*, 44: 119–123 (1995) suggests that IGF-I in conjunction with insulin may provide an additional approach to management of IDDM during adolescence. Mathe, *Biomedicine and Pharmacotherapy*, 49: 221–224 (1995) discloses the role of IGF's in their relation with insulin for treating diabetes mellitus.

As to the patent literature, U.S. Pat. No. 4,988,675 discloses a combination of IGF-I with a lower amount of insulin than normal to treat Type II diabetes. WO 96/01125 published 18 Jan. 1996 discloses the use of a combination of insulin and an IGF-I in the manufacture of a medicament for counteracting a decrease in nitrogen balance and for counteracting a decrease in protein synthesis and which can be used for treatment of a protein catabolism due to glucocorticoid excess. U.S. Pat. No. 5,091,173 discloses a composition suitable for topical application to mammalian skin or hair comprising a cell-free supernatant from a culture of dermal papilla cells sufficient to increase hair growth comprising one or more members of the IGF family selected from IGF-I, IGF-II, and insulin.

The use of an injectable drug other than insulin to treat diabetes, such as IGF-I, is naturally limited due to the desire of diabetics to administer a minimum number of injections. Adding more injections, for IGF-I administration, to regimens that already require several injections per day of insulin is not practical. Further, when combining two proteins such as IGF-I and insulin, it would be necessary to have the resulting formulation stable and well absorbed by the patient, as well as having long-acting insulin. A long-acting insulin regulated in a time- and target-tissue-dependent manner in response to changing demands of the metabolic environment is described by Lewitt et al., *Endocrinology*, 129: 2254–2265 (1991).

Presently, diabetics mix NPH insulin (long-acting neutral protamine hagedorn insulin) with regular insulin. It would be desirable to be able to mix long-acting NPH insulin with IGF-I, each from separate vials in the same syringe, and to inject the mix immediately. It would also be desirable to use the same amount of insulin as is normally used, not a lower than normal amount of insulin, so that it will be most effective in lowering blood glucose levels.

SUMMARY OF THE INVENTION

Accordingly, the present invention provides a parenteral composition comprising IGF-I and NPH insulin in a pharmaceutically acceptable carrier. Preferably, they are present in amounts of from or about 1 to 10 mg IGF-I and from or about 0.2 to 2 mg NPH insulin, preferably at pH from or about 5 to 8, more preferably from or about 5 to 6. Preferably, the amounts of IGF-I and NPH insulin in the composition are from or about 1 to 10 mg/mL each. Also preferred is that the carrier be an acetic acid salt buffer and a phosphate buffer, which carrier contains a sodium counterion and a stabilizer. Additionally preferred is that the composition contain a surfactant, preferably a polysorbate or poloxamer.

In another aspect, the invention provides a composition, preferably for parenteral use, and preferably sterile, comprising IGF-I and NPH insulin in an acetic acid salt buffer.

In a further aspect, the invention provides a composition, preferably for parenteral use, and preferably sterile, comprising IGF-I and NPH insulin in a weight ratio of NPH insulin to IGF-I of from or about 10:1 to 1:50 (w/w), from or about 0.05 to 0.3M of an osmolyte, from or about 0.1 to 10 mg/mL of a stabilizer, from or about 1 to 5 mg/mL of a surfactant, and from or about 5 to 100 mM of a buffer at from or about pH 5 to 7, more preferably 5 to 6.

In a still further aspect, the invention provides a method for treating a hyperglycemic disorder such as diabetes in a mammal comprising administering to the mammal, preferably by either injection or infusion, an effective amount of one of the above compositions.

This invention provides a solution to the problem of dosing IGF-I. It was an unexpected and fortuitous finding that of the many formulations of insulin that are available, only one type, NPH insulin, could be mixed with IGF-I. In addition, unexpected advantages of the dosing of the combination of NPH insulin and IGF-I were discovered upon experimentation as described in detail below.

Moreover, the present invention achieves the goal of being able to mix long-acting NPH insulin and IGF-I, contained in separate vials, in the same syringe, and to inject the mix immediately, and to use the same amount of insulin as is normally used, so that it will be most effective in lowering blood glucose.

BRIEF DESCRIPTION OF THE DRAWINGS

FIG. 6 shows a comparison of rhIGF-I and NPH insulin subcutaneous (SC) injections in STZ diabetic rats, by depicting a graph of plasma glucose versus time for the control (open circles with solid line), rhIGF-I (open circles with dotted line), NPH insulin (open triangles), two separate injections of rhIGF-I and NPH insulin (open squares), and a single injection of rhIGF-I and NPH insulin (open/solid squares).

DESCRIPTION OF THE PREFERRED EMBODIMENTS

A. Definitions

Figure 1A:
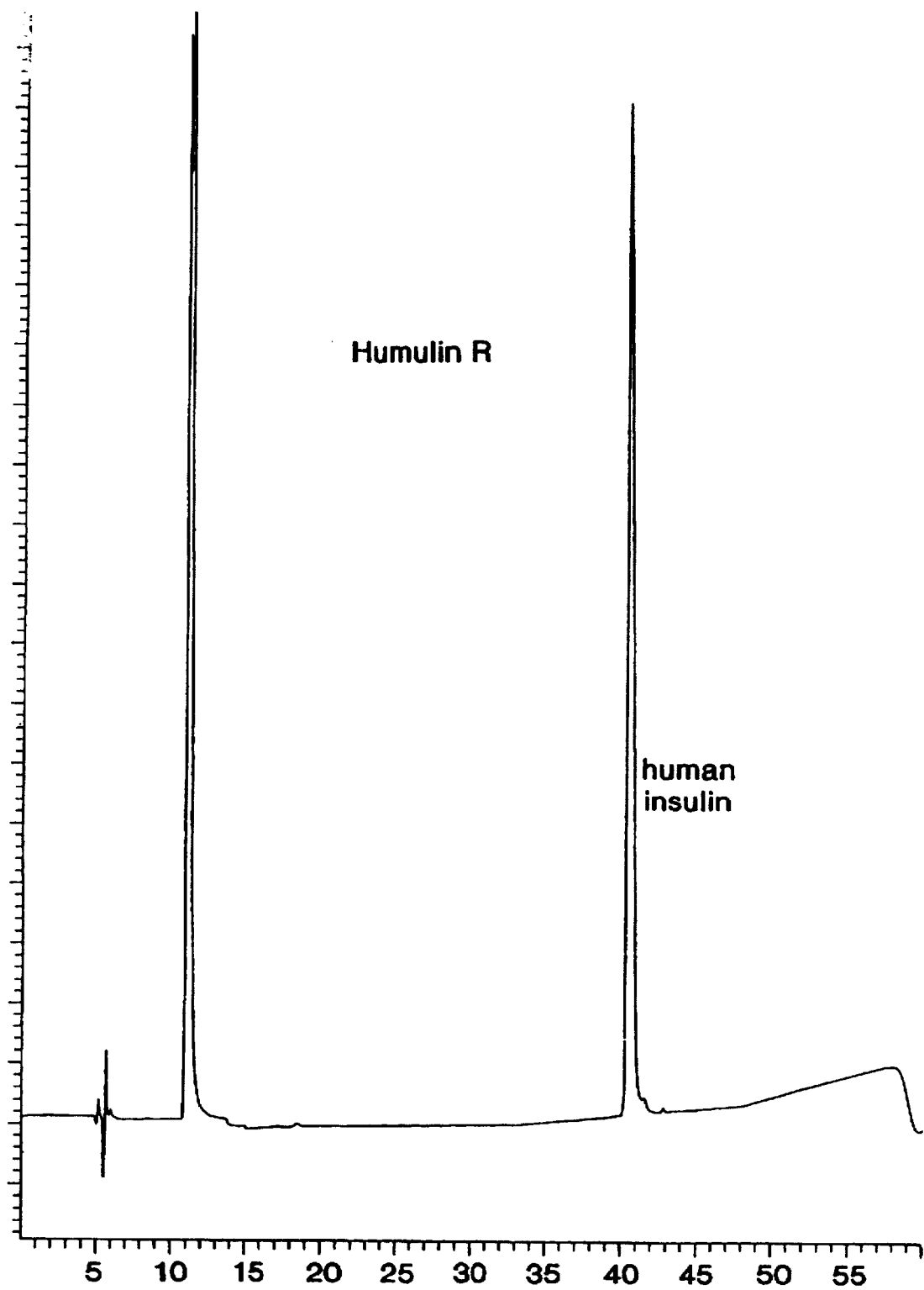
FIG. 1A depicts an acidic pH reversed-phase chromatogram of HUMULIN® R brand insulin.

As used herein, "mammal" for purposes of treatment refers to any animal classified as a mammal, including humans, domestic, and farm animals, and zoo, sports, or pet animals, such as dogs, horses, cats, sheep, pigs, cows, etc. The preferred mammal herein is a human. The term "non-adult" refers to mammals that are from perinatal age (such as low-birth-weight infants) up to the age of puberty, the latter being those that have not yet reached full growth potential.

As used herein, "IGF-I" refers to insulin-like growth factor from any species, including bovine, ovine, porcine, equine, and preferably human, in native-sequence or in variant form, and from any source, whether natural, synthetic, or recombinant. Preferred herein for animal use is that form of IGF-I from the particular species being treated, such as porcine IGF-I to treat pigs, ovine IGF-I to treat sheep, bovine IGF-I to treat cattle, etc. Preferred herein for human use is human native-sequence, mature IGF-I, more preferably without a N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif. for clinical investigations.

The preferred IGF-I variants are those described in U.S. Pat. Nos. 5,077,276; 5,164,370; or 5,470,828; or in WO 87/01038, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-I, des(1-3)-IGF-I, or des-IGF-I).

As used herein, "NPH insulin" refers to neutral protamine hagedorn insulin, otherwise known as "isophane," from any species, including bovine, ovine, porcine, equine, and preferably human, and from any source, whether natural, synthetic, or recombinant. Preferred herein for animal use is that form of NPH insulin from the particular species being treated, such as human NPH insulin to treat humans. Preferred NPH insulin for human use is NPH insulin sold commercially by Novo-Nordisk under the trademark INSULATAR™ or by Eli-Lilly under the trademark HUMULIN N™. All NPH insulin drugs reported in *Diabetes Mellitus—Theory and Practice*, fourth edition, Harold Rifkin, MD, Ed. (Elsevier, New York, 1990), Chapter 29, and *U.S. Pharmacist*, 18 (November Suppl.) p. 38–40 (1993) are suitable herein.

As used herein, the term "hyperglycemic disorders" refers to all forms of diabetes, such as type I and type II diabetes, as well as hyperinsulinemia and hyperlipidemia, e.g., obese subjects, and insulin-resistant diabetes, such as Mendenhall's Syndrome, Werner Syndrome, leprechaunism, lipoatrophic diabetes, and other lipoatrophies. The preferred hyperglycemic disorder is diabetes, especially type I and type II diabetes. "Diabetes" itself refers to a progressive disease of carbohydrate metabolism involving inadequate production or utilization of insulin and is characterized by hyperglycemia and glycosuria.

As used herein, the term "treating" refers to both therapeutic treatment and prophylactic or preventative measures. Those in need of treatment include those already with the disorder as well as those prone to having the disorder or diagnosed with the disorder or those in which the disorder is to be prevented. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature. The treatment regime herein can be either consecutive or intermittent, but preferably is consecutive when both proteins are formulated and administered together.

As used herein, the term "hypoglycemic agent" refers to secretagogues, preferably oral agents, excluding insulin, which cause the secretion of insulin by the pancreas. More preferred herein for human use are the sulfonylurea class of oral hypoglycemic agents. Examples include glyburide, glipizide, and gliclazide. In addition, agents that enhance insulin sensitivity, such as biguanides, are within this definition, and also are preferred.

B. Modes for Carrying Out the Invention

The IGF-I and NPH insulin are combined and directly administered to the mammal by any suitable technique, including infusion and injection. The specific route of administration will depend, e.g., on the medical history of the patient, including any perceived or anticipated side effects using NPH insulin or IGF-I alone, and the particular disorder to be corrected. Examples of parenteral administration include subcutaneous, intramuscular, intravenous, intraarterial, and intraperitoneal administration. Most preferably, the administration is by continuous infusion (using, e.g., slow-release devices or minipumps such as osmotic pumps or skin patches), or by injection (using, e.g., intravenous or subcutaneous means). Preferably, the administration is subcutaneous injection for the mixture. The administration may also be as a single bolus or by slow-release depot formulation. Delivery of NPH insulin and IGF-I by injection will be the preferred form of administration for treating diabetes.

The IGF-I and NPH insulin composition to be used in the therapy will be formulated and dosed in a fashion consistent with good medical practice, taking into account the clinical condition of the individual patient (especially the side effects of treatment with NPH insulin or IGF-I alone), the site of delivery of the IGF-I and NPH insulin composition, the method of administration, the scheduling of administration, and other factors known to practitioners. The "effective amounts" of each component for purposes herein are thus determined by such considerations and must be amounts that result in bioavailability of the drugs to the mammal and blood glucose lowering effect.

As a general proposition, the total pharmaceutically effective amount of the IGF-I and NPH insulin administered parenterally per dose will be in the range of from or about 10 µg/kg/day to 200 µg/kg/day of IGF-I based on kg of patient body weight, and from or about 0.5 to 500 units/day of NPH insulin, although, as noted above, this will be subject to a great deal of therapeutic discretion. Preferably for treatment of diabetes in humans, the dose of IGF-I is from or about 1 to 10 mg twice per day, more preferably from or about 20 to 80 µg/kg/injection (i.e., from or about 1.5 to 6 mg) twice a day subcutaneously, and the dose of NPH insulin is from or about 5 to 50 units/injection (i.e., from or about 0.2 to 2 mg) twice a day subcutaneously. The ratio of NPH insulin to IGF-I in this formulation by weight is generally from or about 10:1 to 1:50, preferably from or about 1:1 to 1:20, more preferably from or about 1:1 to 1:10, still more preferably, from or about 1:1 to 1:5, and most preferably from or about 1:1 to 1:3.

Although injection is preferred, an infusion device may also be employed for continuous SC infusions. An intravenous bag solution may also be employed. The key factor in selecting an appropriate dose is the result obtained, as measured by decreases in blood glucose so as to approximate the normal range, or by other criteria for measuring treatment of diabetes as defined herein as are deemed appropriate by the practitioner. Further information on dosing NPH insulin can be found in *Diabetes Mellitus—Theory and Practice*, supra, Chapters 29 and 30.

In another embodiment for administering the combination of IGF-I and NPH insulin, the insulin administration is continuous and the IGF-I is administered to the mammal in an intermittent fashion so as to sustain its biological response in the treatment of diabetes. This is accomplished usually by administering a therapeutically effective amount of the IGF-I to the mammal to provide an exposure to IGF-I and NPH insulin for a period of time that provides the maximum biological response in the mammal, then discontinuing the administration of the IGF-I (but not the NPH insulin) for a period of time equal to or less than the time period during which the IGF-I was previously administered, then administering a therapeutically effective amount of IGF-I (with NPH insulin administration continuing) to the mammal to provide an exposure to IGF-I and NPH insulin for a period of time that provides the maximum biological response in the mammal, then discontinuing the administration of the IGF-I (but not the NPH insulin) for a period of time equal to or less than the time period during which the IGF-I was just previously administered, and repeating this pattern of administration and discontinuance of administration of IGF-I for as long as necessary to achieve or maintain sustained biological response in the mammal.

Also, the formulation herein is suitably administered along with an IGF binding protein, for example, one of those currently known, i.e., IGFBP-1, IGFBP-2, IGFBP-3, IGFBP-4, IGFBP-5, or IGFBP-6, or with the ALS of the IGF binding complex. Such proteins may be administered separately or as a complex with the IGF-I. The IGF-I may also be coupled to a receptor or antibody or antibody fragment for administration. The preferred binding protein for IGF-I herein is IGFBP3, which is described in U.S. Pat. No. 5,258,287 and by Martin and Baxter, *J. Biol. Chem.*, 261: 8754–8760 (1986). This glycosylated IGFBP3 protein is an acid-stable component of about 53 Kd on a non-reducing SDS-PAGE gel of a 125–150 Kd glycoprotein complex found in human plasma that carries most of the endogenous IGFs and is also regulated by GH.

The administration of the IGF binding protein with IGF-I and NPH insulin may be accomplished by the method described in U.S. Pat. No. 5,187,151. Briefly, the IGF-I and IGFBP are administered in effective amounts by subcutaneous bolus injection in a molar ratio of from or about 0.5:1 to 3:1, preferably about 1:1; the NPH insulin is already present with the IGF-I.

Furthermore, the formulation is suitably administered along with an effective amount of a hypoglycemic agent such as a sulfonylurea. The hypoglycemic agent is administered to the mammal by any suitable technique including parenterally, intranasally, orally, or by any other effective route. Most preferably, the administration is by the oral route. For example, MICRONASEM™ tablets (glyburide) marketed by Upjohn in 1.25, 2.5, and 5 mg tablet concentrations are suitable for oral administration. The usual maintenance dose for Type II diabetics, placed on this therapy, is generally in the range of from or about 1.25 to 20 mg per day, which may be given as a single dose or divided throughout the day as deemed appropriate [*Physician's Desk Reference*, 2563–2565 (1995)]. Other examples of glyburide-based tablets available for prescription include GLYNASE™ brand drug (Upjohn) and DIABETA™ brand drug (Hoechst-Roussel). GLUCOTROLE™ (Pratt) is the trademark for a glipizide(1-cyclohexyl-3-[p-[2-(5- methylpyrazine carboxamide)ethyl]phenyl]sulfonyl]urea) tablet available in both 5 and 10 mg strengths and is also prescribed to Type II diabetics who require hypoglycemic therapy following dietary control or in patients who have ceased to respond to other sulfonylureas [*Physician's Desk Reference*, 1902–1903 (1995)]. Other hypoglycemic agents than sulfonylureas, such as the biguanides (e.g., metformin and phenformin) or troglitozones, or other drugs affecting insulin action may also be employed.

The IGF-I and NPH insulin are also suitably administered together by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman et al., *Biopolymers*, 22, 547–556 [1983]), poly(2-hydroxyethyl methacrylate) (Langer et al., *J. Biomed. Mater. Res.*, 15: 167–277 (1981), and Langer, *Chem. Tech.*, 12: 98–105 [1982]), ethylene vinyl acetate (Langer et al., supra) or poly-D-(−)-3-hydroxybutyric acid (EP 133,988). Sustained-release IGF-I compositions also include liposomally entrapped IGF-I. Liposomes containing IGF-I are prepared by methods known per se: DE 3,218,121; Epstein et al., *Proc. Natl. Acad. Sci. U.S.A.*, 82: 3688–3692 (1985); Hwang et al., *Proc. Natl. Acad. Sci. U.S.A.*, 77: 4030–4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol. percent cholesterol, the selected proportion being adjusted for the optimal IGF-I and NPH insulin therapy.

For parenteral administration, in one embodiment, the IGF-I and NPH insulin are formulated generally by mixing each at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IGF-I and NPH insulin each uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc.

The IGF-I and NPH insulin are typically formulated in such vehicles at a pH of from or about 4.5 to 8. Full-length IGF-I is generally stable at a pH of no more than about 6.5; des(1-3)-IGF-I is stable at from or about 3.2 to 5. It will be understood that use of certain of the foregoing excipients, carriers, or stabilizers will result in the formation of IGF-I or insulin salts. The final preparation may be a stable liquid or lyophilized solid.

In one particularly preferred embodiment for treating diabetes, the composition comprises IGF-I and NPH insulin in a weight ratio of NPH insulin:IGF-I of from or about 10:1 to 1:50 (w/w), from or about 0.05 to 0.3M of an osmolyte, preferably an inorganic salt and/or sugar alcohol, from or about 0.1 to 10 mg/mL of at least one stabilizer, from or about 1 to 5 mg/mL of a surfactant, and from or about 5 to 100 mM of a buffer at from or about pH 5 to 7, preferably 5 to 6. The more preferred amounts of IGF-I and NPH insulin in this composition are from or about 1 to 10 mg IGF-I and from or about 0.2 to 2 mg NPH insulin in each injection. The more preferred weight ratio of NPH insulin:IGF-I is from or about 1:1 to 1:20, more preferably from or about 1:1 to 1:10, still more preferably from or about 1:1 to 1:5, and most preferably from or about 1:1 to 1:3.

An "osmolyte" refers to an isotonic modifier or osmotic adjuster that lends osmolality to the buffered solution. Osmolality refers to the total osmotic activity contributed by ions and non-ionized molecules to a solution. Examples include inorganic salts such as sodium chloride and potassium chloride, mannitol, PEG, polypropylene glycol, glycine, sucrose, trehalose, glycerol, amino acids, and sugar alcohols such as mannitol known to the art that are generally regarded as safe (GRAS). The preferred osmolyte herein is sodium chloride or potassium chloride.

The "stabilizer" is any compound that functions to preserve the active ingredients in the formulation, i.e., NPH insulin and IGF-I, so that they do not degrade or otherwise become inactive over a reasonable period of time or develop pathogens or toxins that prevent their use. Examples of stabilizers include preservatives that prevent bacteria, viruses, and fungi from proliferating in the formulation, anti-oxidants, or other compounds that function in various ways to preserve the stability of the formulation.

For example, quaternary ammonium salts are useful stabilizers in which the molecular structure includes a central nitrogen atom joined to four organic (usually alkyl or aryl) groups and a negatively charged acid radical. These salts are useful as surface-active germicides for many pathogenic non-sporulating bacteria and fungi and as stabilizers. Examples include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of stabilizers include aromatic alcohols such as phenol and benzyl alcohol, alkyl parabens such as methyl or propyl paraben, and m-cresol. The most preferred stabilizer herein is phenol or benzyl alcohol.

The stabilizer is included in a stable liquid form of the NPH insulin and IGF-I formulation, but not in a lyophilized form of the formulation. In the latter case, the stabilizer is present in the bacteriostatic water for injection (BWFI) used for reconstitution. The surfactant is also optionally present in the reconstitution diluent.

The "inorganic salt" is a salt that does not have a hydrocarbon-based cation or anion. Examples include sodium chloride, ammonium chloride, potassium chloride, magnesium chloride, calcium chloride, sodium phosphate, calcium phosphate, sodium sulfate, potassium phosphate, ammonium phosphate, sodium sulfate, ammonium sulfate, potassium sulfate, magnesium sulfate, calcium sulfate, etc. Preferably, the cation is sodium and the anion is chloride or sulfate, and the most preferred inorganic salt is potassium chloride or sodium chloride.

The "surfactant" acts to increase the solubility of the IGF-I and NPH insulin at a pH from or about 4 to 7. It is preferably a nonionic surfactant such as a polysorbate, e.g., polysorbates 20, 60, or 80, a poloxamer, e.g., poloxamer 184 or 188, or any others known to the art that are GRAS. More preferably, the surfactant is a polysorbate or poloxamer, more preferably a polysorbate, and most preferably polysorbate 20.

The "buffer" may be any suitable buffer that is GRAS and generally confers a pH from or about 4.8 to 8, preferably from or about 5 to 7, more preferably from or about 5 to 6, on the NPH insulin+IGF-I formulation, and preferably a pH of from or about 5 to 6, more preferably from or about 5 to 5.5, on the IGF-I formulation. Examples include acetic acid salt buffer, which is any salt of acetic acid, including sodium acetate and potassium acetate, succinate buffer, phosphate buffer, citrate buffer, histidine buffer, or any others known to the art to have the desired effect. The most preferred buffer is sodium acetate, optionally in combination with sodium phosphate.

The most preferred composition containing both IGF-I and NPH insulin is the following: a weight ratio of NPH insulin:IGF-I of from or about 1:1 to 1:3, from or about 5 to 7 mg/mL of sodium chloride, from or about 0.1 to 3 mg/mL of phenol and/or from or about 6 to 10 mg/mL of benzyl alcohol, from or about 1 to 3 mg/mL of polysorbate, from or about 2.5 to 4 mg/mL of sodium acetate, and from or about 0.1 to 1 mg/mL of sodium phosphate, pH about 5.4.

The final formulation, if a liquid, is preferably stored at a temperature of from or about 2° to 8° C. for up to about four weeks. Alternatively, the formulation can be lyophilized and provided as a powder for reconstitution with water for injection that is stored as described for the liquid formulation.

IGF-I and NPH insulin to be used for therapeutic administration must be sterile. Sterility is readily accomplished by filtration through sterile filtration membranes (e.g., 0.26 micron membranes). Therapeutic IGF-I and NPH insulin compositions generally are placed into a container having a sterile access port, for example, an intravenous solution bag or vial having a stopper pierceable by a hypodermic injection needle.

IGF-I and NPH insulin ordinarily will be stored in unit or multi-dose containers, for example, in sealed ampules or vials, as an aqueous solution, or as a lyophilized formulation for reconstitution. As an example of a lyophilized formulation, 10-mL vials are filled with 5 mL of sterile-filtered 1% (w/v) aqueous NPH insulin solution, and the resulting mixture is lyophilized. The infusion solution is prepared by reconstituting the lyophilized NPH insulin using bacteriostatic Water-for-Injection. This infusion solution is then mixed with a similarly reconstituted IGF-I solution or a liquid IGF-I solution.

The formulation containing both the IGF-I and NPH insulin can be made by many different methods. One method comprises mixing NPH insulin with an IGF-I-containing composition (having osmolyte, stabilizer, and buffer as described below).

The IGF-I-containing solution useful for administering IGF-I separately from NPH insulin and for admixing with the NPH insulin solution as described above is as follows: from or about 2 to 20 mg/mL of IGF-I, from or about 2 to 50 mg/mL of an osmolyte, from or about 1 to 15 mg/mL of at least one stabilizer, and a buffer (preferably an acetic acid salt buffer, and most preferably sodium acetate) in an amount such that the composition has a pH of from or about 5 to 5.5. The osmolyte, stabilizer, and buffer, and the preferred compounds within these categories are defined above. Optionally, the formulation may also contain a surfactant selected from the types described above, preferably in an amount of from or about 1 to 5 mg/mL, more preferably from or about 1 to 3 mg/mL.

In a preferred embodiment, the osmolyte is an inorganic salt at a concentration of from or about 2 to 10 mg/mL or a sugar alcohol at a concentration of from or about 40 to 50 mg/mL, the stabilizer is benzyl alcohol, phenol, or both, and the buffered solution is an acetic acid salt buffered solution. More preferably, the osmolyte is an inorganic salt, most preferably sodium chloride.

In an even more preferred formulation, the amount of IGF-I is from or about 8 to 12 mg/mL, the amount of sodium chloride is from or about 5 to 6 mg/mL, the stabilizers are benzyl alcohol in an amount of from or about 8 to 10 mg/mL and/or phenol in an amount of from or about 2 to 3 mg/mL, and the buffer is about 50 mM sodium acetate so that the pH is about 5.4. In this formulation, the preferred amount of NPH insulin is about 100 units/mL, or about 4 mg/mL. The volumes of drugs can be varied or the concentration of NPH insulin can be fixed. Optionally, the formulation contains polysorbate as a surfactant in an amount of from or about 1 to 3 mg/mL. A 50-mM acetate concentration in the starting IGF-I solution before mixing with NPH insulin ensures that the final pH will not vary significantly from 5.4 in the final IGF-I/NPH insulin mixture to maintain high solubility of IGF-I and low solubility of NPH insulin as a suspension over a wide mixing ratio range. However, a broader pH range in terms of stability of both proteins is from or about 4.5 to 8.

Kits are also contemplated for this invention. A typical kit would comprise a container, preferably a vial, for the IGF-I formulation comprising IGF-I in a pharmaceutically acceptable acetic acid salt buffer, a container, preferably a vial, comprising pharmaceutically acceptable NPH insulin, and instructions, such as a product insert or label, directing the user to combine the contents of the two containers, i.e., the two formulations, to provide a pharmaceutical formulation. Preferably, the pharmaceutical formulation is for treating diabetes. Also, preferably the container with IGF-I additionally comprises sodium chloride and benzyl alcohol or phenol, or both, in the buffer at a pH of from or about 5.0 to 5.5. Preferably, the user will be instructed to combine the contents of the containers, i.e., the two formulations, in a syringe for immediate injection.

In another preferred embodiment, the container with IGF-I comprises from or about 8 to 12 mg/mL of IGF-I, from or about 5 to 6 mg/mL of sodium chloride, from or about 8 to 10 mg/mL of benzyl alcohol or from or about 2 to 3 mg/mL of phenol, or both from or about 8 to 10 mg/mL of benzyl alcohol and from or about 2 to 3 mg/mL of phenol, in an about 50 mM sodium acetate buffered solution at a pH of about 5.4. More preferably, this container further comprises from or about 1 to 3 mg/mL polysorbate.

The invention will be more fully understood by reference to the following examples. They should not, however, be construed as limiting the scope of the invention. All literature and patent citations mentioned herein are expressly incorporated by reference.

EXAMPLE I

MATERIALS

| 1) | IGF-I | 10.0 mg/mL |
|---|---|---|
| | Sodium chloride | 5.84 mg/mL |
| | Sodium acetate | 50 mM, pH 5.4 |
| | Benzyl alcohol | 9.0 mg/mL |
| | Polysorbate 20 | 2.0 mg/mL |

2) HUMULIN® R (regular insulin human injection, USP, recombinant DNA origin)
3) HUMULIN® N (NPH human insulin, recombinant DNA origin, isophane suspension)
4) NOVOLIN® N (NPH human insulin, recombinant DNA origin, isophane suspension)
5) HUMULIN® L (Lente human insulin, recombinant DNA origin, zinc suspension)
6) NOVOLIN® L (Lente human insulin, recombinant DNA origin, zinc suspension)
7) HUMULIN® U (Ultralente, human insulin, recombinant DNA origin, extended zinc suspension)

METHODS

Mixing

One volume of human insulin was mixed with an equal volume of IGF-I using the following procedure:

1) Draw air into syringe equal to the amount of human insulin for mixing. Insert the needle into the human insulin bottle and inject air. Withdraw the needle.
2) Inject air into the IGF-I bottle in the same manner, but do not withdraw the needle.
3) Turn the bottle and syringe upside down.
4) Make sure the tip of the needle is in the IGF-I, withdraw the correct dose of IGF-I into the syringe.
5) Before removing the needle from the bottle, check the syringe for air bubbles which reduce the amount of IGF-I in it. If bubbles are present, hold the syringe straight up and tap its sides until the bubbles float to the top. Push them out with the plunger and withdraw the correct dose.
6) Remove the needle from the bottle of IGF-I and insert it into the bottle of human insulin. Turn the bottle and syringe upside down. Hold the bottle and syringe firmly in one hand and shake gently (no shaking for regular human insulin). Make sure the tip of the needle is in the insulin, withdraw the dose of human insulin.
7) Remove the needle.

Sample preparation for HPLC analysis (a) HUMULIN® N, NOVOLIN® N, HUMULIN® L, NOVOLIN® L, and HUMULIN® U Human insulin was gently inverted several times to mix the suspension. Approximately 1 mL of sample was withdrawn into an insulin syringe. The insulin was discharged into a centrifuge tube, then centrifuged at 3000 r.p.m. for 10 minutes. The centrifuge step was designed to remove human insulin suspension from solution. After centrifugation, the insulin sample was filtered through a 0.22 µm filter to further remove human insulin suspension. After filtration the solution was analyzed by using the acidic pH reversed-phase HPLC method described below:

solvent A: 0.1% trifluoroacetic acid
solvent B: 0.1% trifluoroacetic acid in acetonitrile
flow rate: 0.5 mL/minute
column temperature: 50° C.
wavelength: 214 nm
injection volume: 25 µg/injection
column: VYDAC® C18 HPLC column, 4.6×250 cm, 300 Å

(b) HUMULINO® R

This solution was analyzed by the above HPLC method with no sample preparation step.

(c) IGF-I

IGF-I was diluted to 1 mg/mL using IGF-I placebo. The diluted sample was analyzed by the above HPLC method.

(d) Human insulin/IGF-I mixture

Human insulin was mixed with IGF-I in an insulin syringe using the mixing method described above. Immediately after mixing, the mixture was injected into a centrifuge tube, then gently vortexed for 1–2 seconds. After vortexing, the mixture was centrifuged at 3000 r.p.m. for 10 minutes, then filtered through a 0.22 µm filter to remove human insulin suspension. The filtered sample was then analyzed by the acidic pH reversed-phase HPLC method described above.

RESULTS

The results are shown in Table I below:

TABLE I

| | Before Mixing | After Mixing |
| | | |
| Sample | Color pH and Appearance | Color pH and Appearance |
|---|---|---|
| IGF-I | 5.4 colorless, clear solution | N/A N/A[1] |
| HUMULIN ® R | 7.3 colorless, clear solution | 5.4 cloudy suspension |
| HUMULIN ® N | 7.0 cloudy suspension | 6.1 cloudy suspension |
| NOVOLIN ® N | 7.2 cloudy suspension | 6.2 cloudy suspension |
| HUMULIN ® L | 7.1 cloudy suspension | 5.6 cloudy suspension |
| NOVOLIN ® L | 7.3 cloudy suspension | 5.6 cloudy suspension |
| HUMULIN ® U | 7.2 cloudy suspension | 5.7 cloudy suspension |

[1]N/A means not applicable.

DISCUSSION

HUMULINO® R

Immediately after mixing HUMULIN® R with IGF-I, the pH of the solution was changed from 7.3 to 5.4 (see Table I), because HUMULIN® R is not buffered. Since human insulin is least soluble at its isoelectric pH (pH 5.4), it became insoluble and the mixture turned cloudy. Approximately 95% of total human insulin and 25% IGF-I became precipitated. The data indicate that HUMULIN® R is not compatible with IGF-I.

HUMULIN® N and NOVOLIN® N (NPH)

Figure 1B:
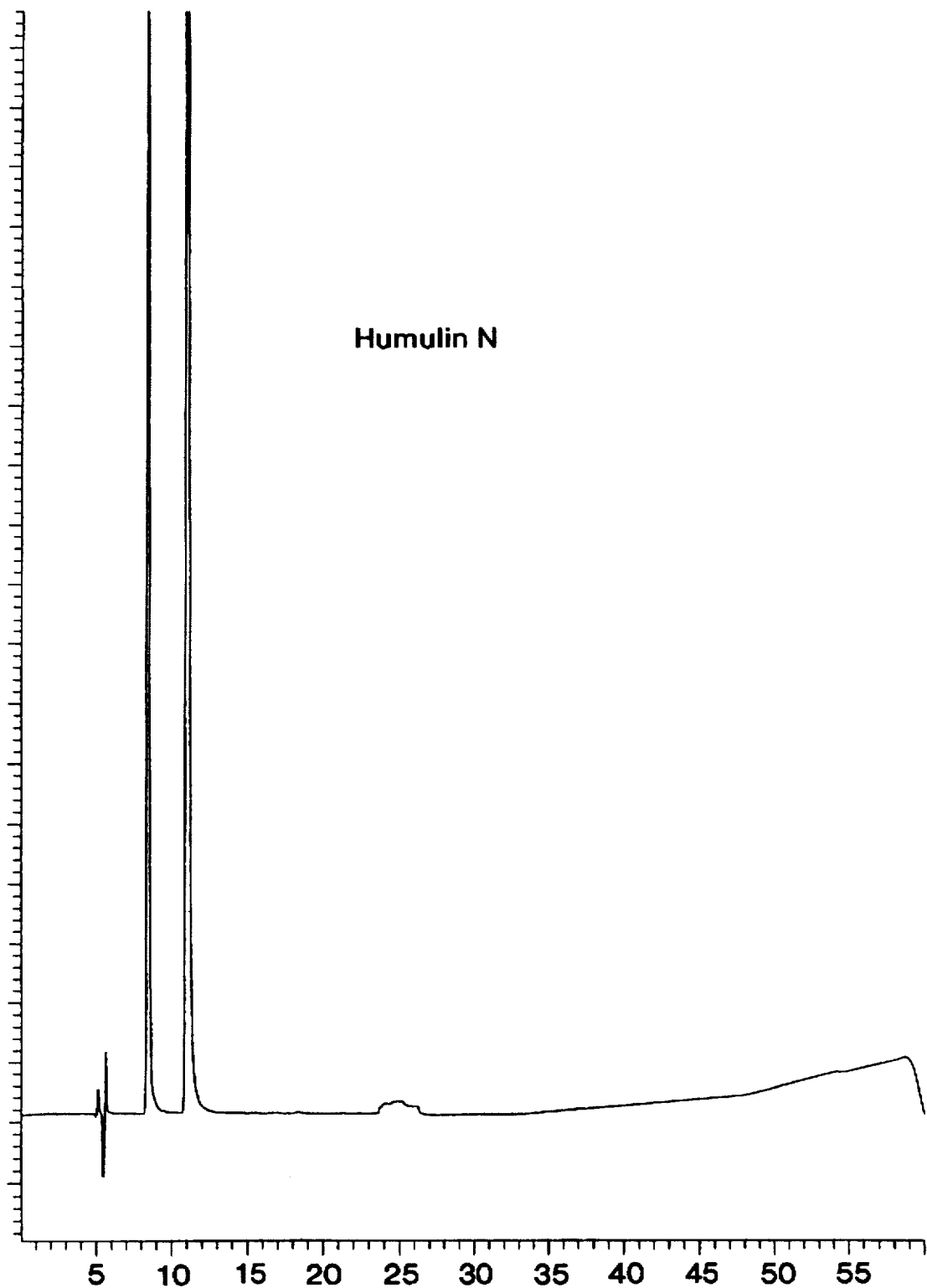
FIG. 1B depicts an acidic pH reversed-phase chromatogram of HUMULIN® N brand insulin.
Figure 1C:
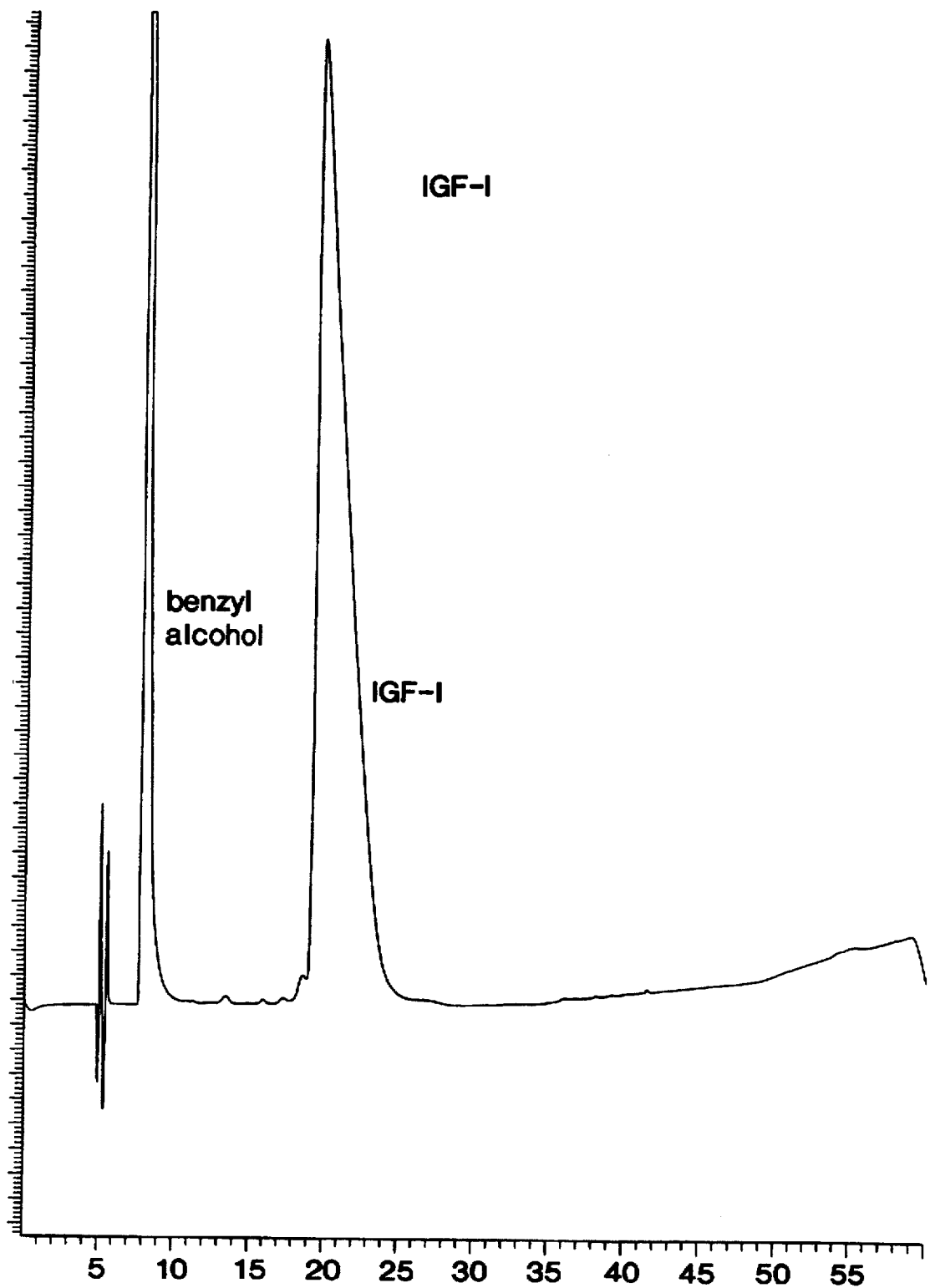
FIG. 1C depicts an acidic pH reversed-phase chromatogram of IGF-I.

After addition of IGF-I, there was no observable change in HUMULIN® N crystals. FIG. 1A shows that on an acidic pH reversed-phase chromatogram of HUMULIN® R, human insulin elutes at 41 minutes. FIG. 1B, which is an acidic pH reversed-phase chromatogram of HUMULIN® N, shows that no human insulin was present in the solution. Human insulin in HUMULIN® N is present only as insoluble crystals. These crystals were removed by centrifugation and filtration. FIG. 1C, which is an acidic pH reversed-phase chromatogram of IGF-I in the formulation indicated below in Example II, shows that approximately 99% of IGF-I is intact and unoxidized and elutes at 22 minutes.

Figure 2A:
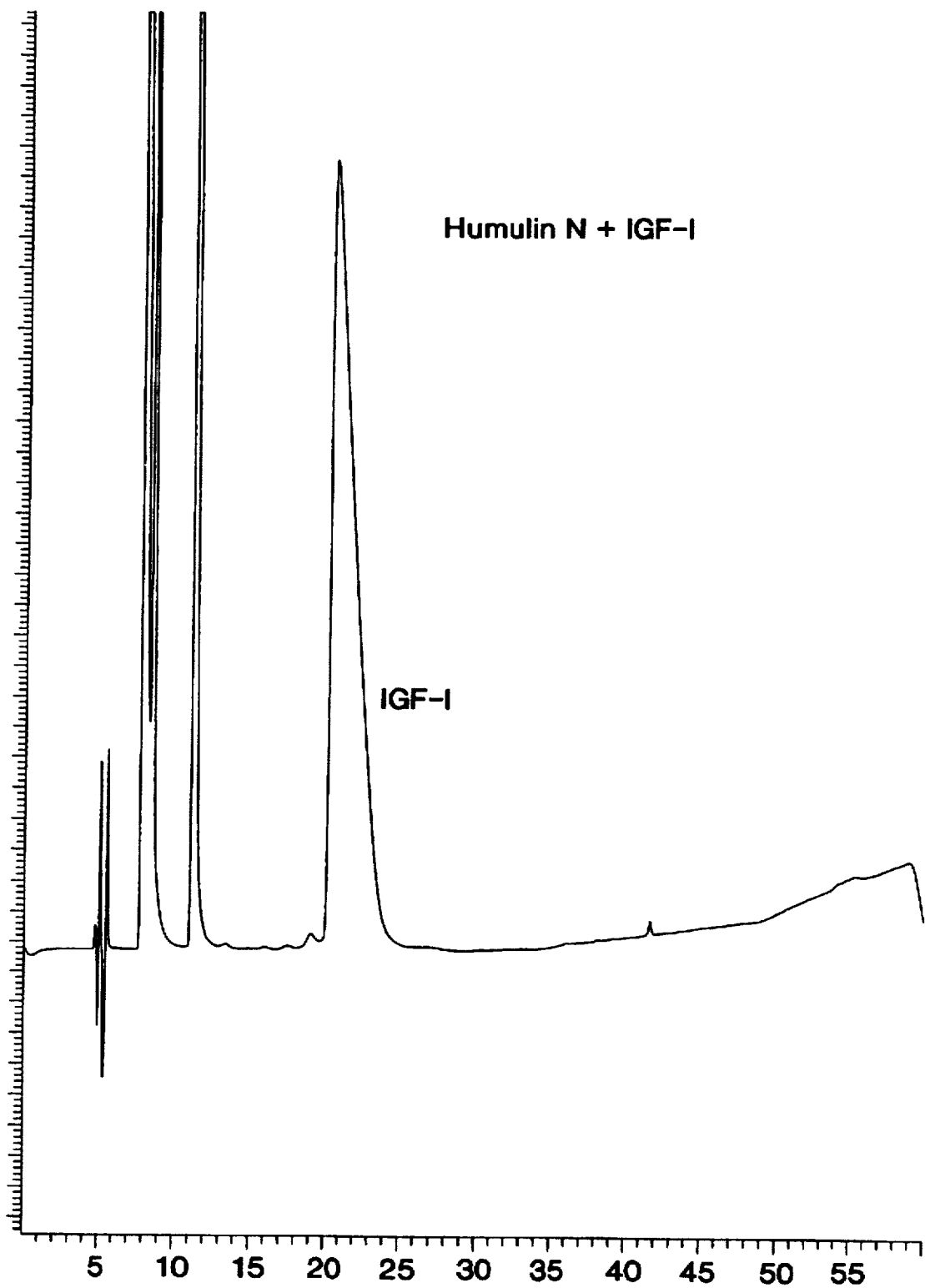
FIG. 2A depicts an acidic pH reversed-phase chromatogram of HUMULIN® N brand insulin plus IGF-I.
Figure 2B:
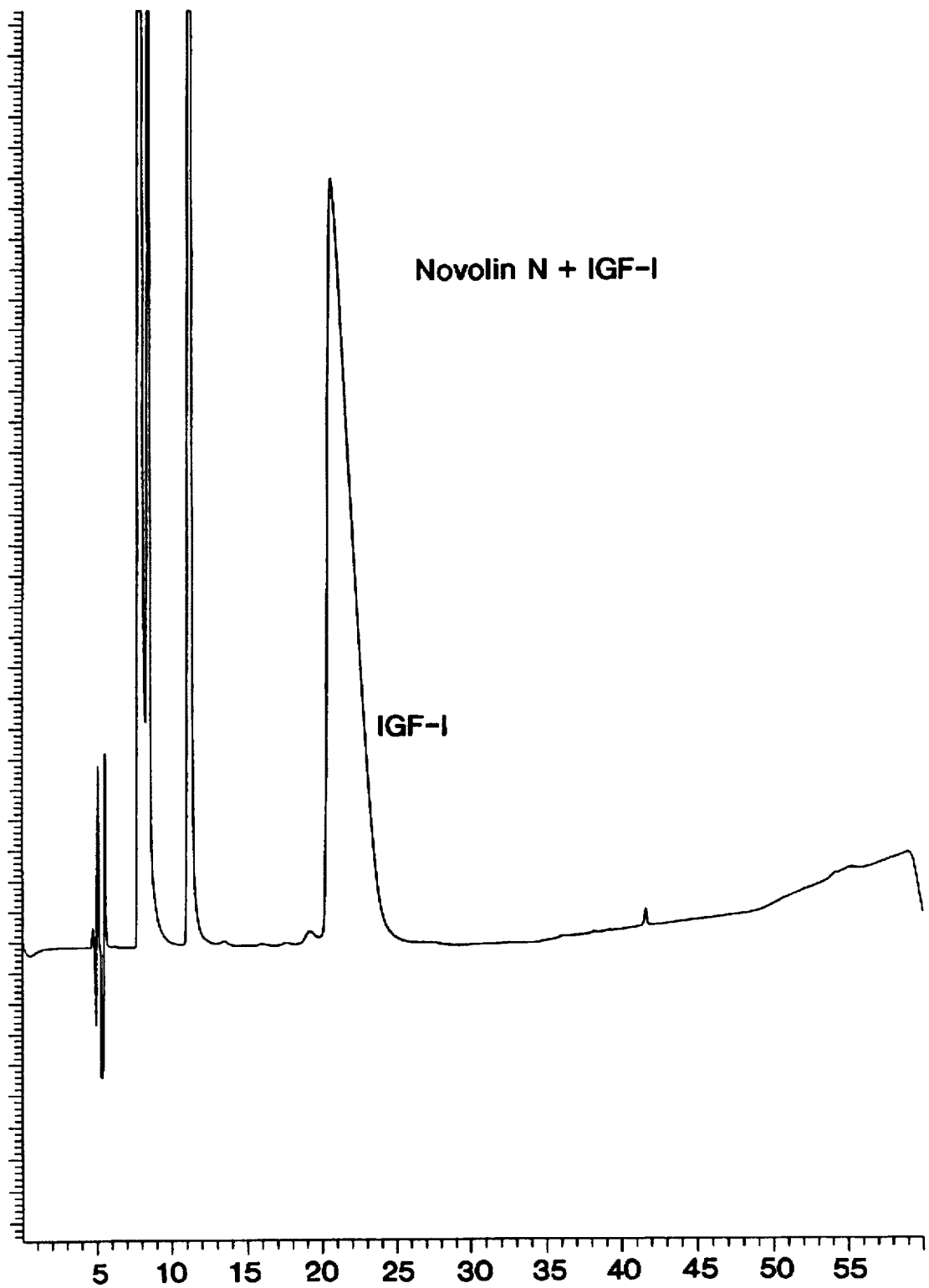
FIG. 2B depicts an acidic pH reversed-phase chromatogram of NOVOLIN® N brand insulin plus IGF-I.

FIGS. 2A and 2B represent acidic pH reversed-phase chromatograms of HUMULIN® N and NOVOLIN® N, respectively, combined with IGF-I. After addition of IGF-I, human insulin remains crystalline. No human insulin was present in the solution. The peak area and shape of IGF-I remain unchanged in the mixture of HUMULIN® N or NOVOLIN® N.

HUMULIN® U (Ultra Lente)

Figure 3A:
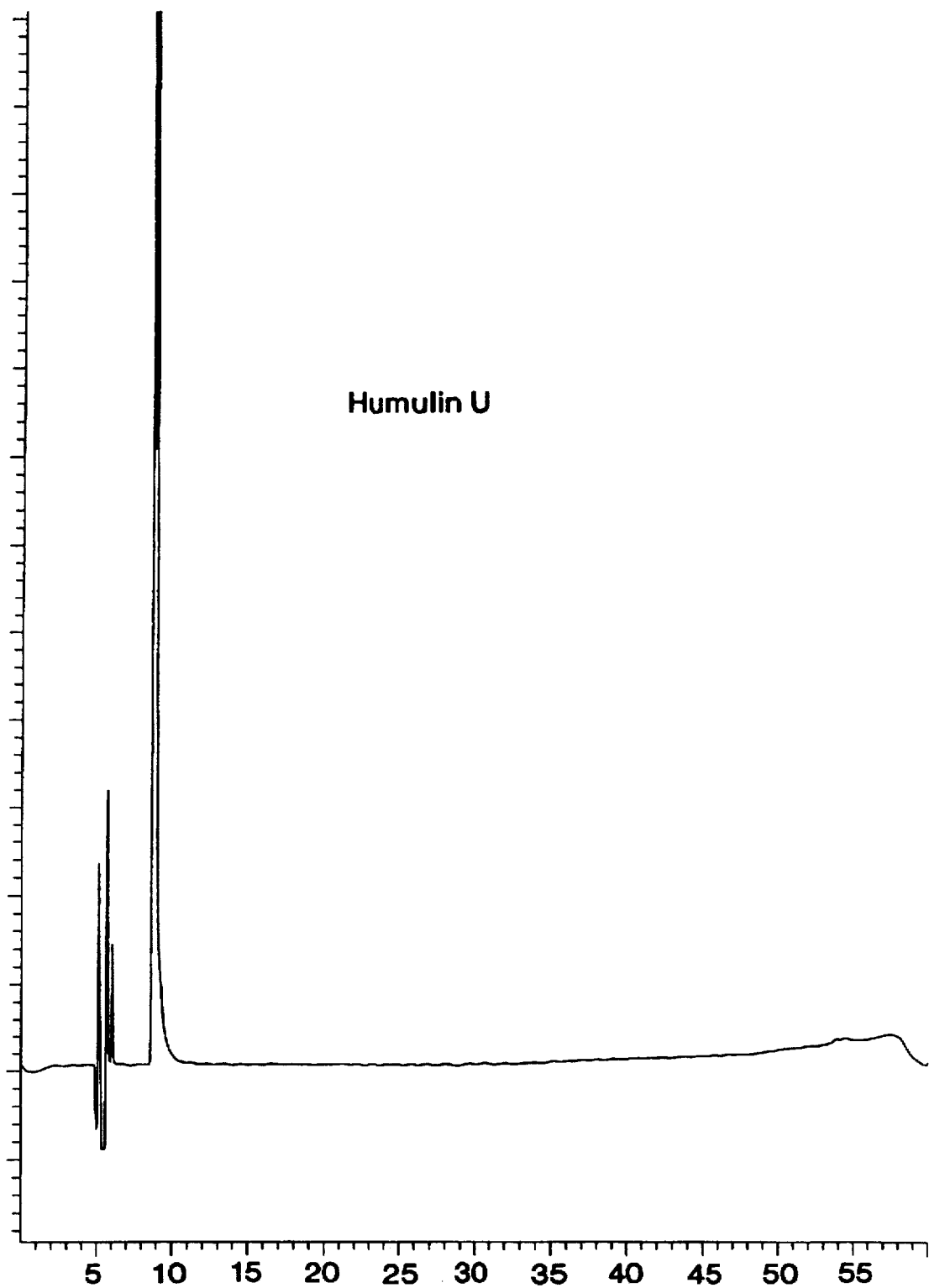
FIG. 3A depicts an acidic pH reversed-phase chromatogram of HUMULIN® U brand insulin.
Figure 3B:
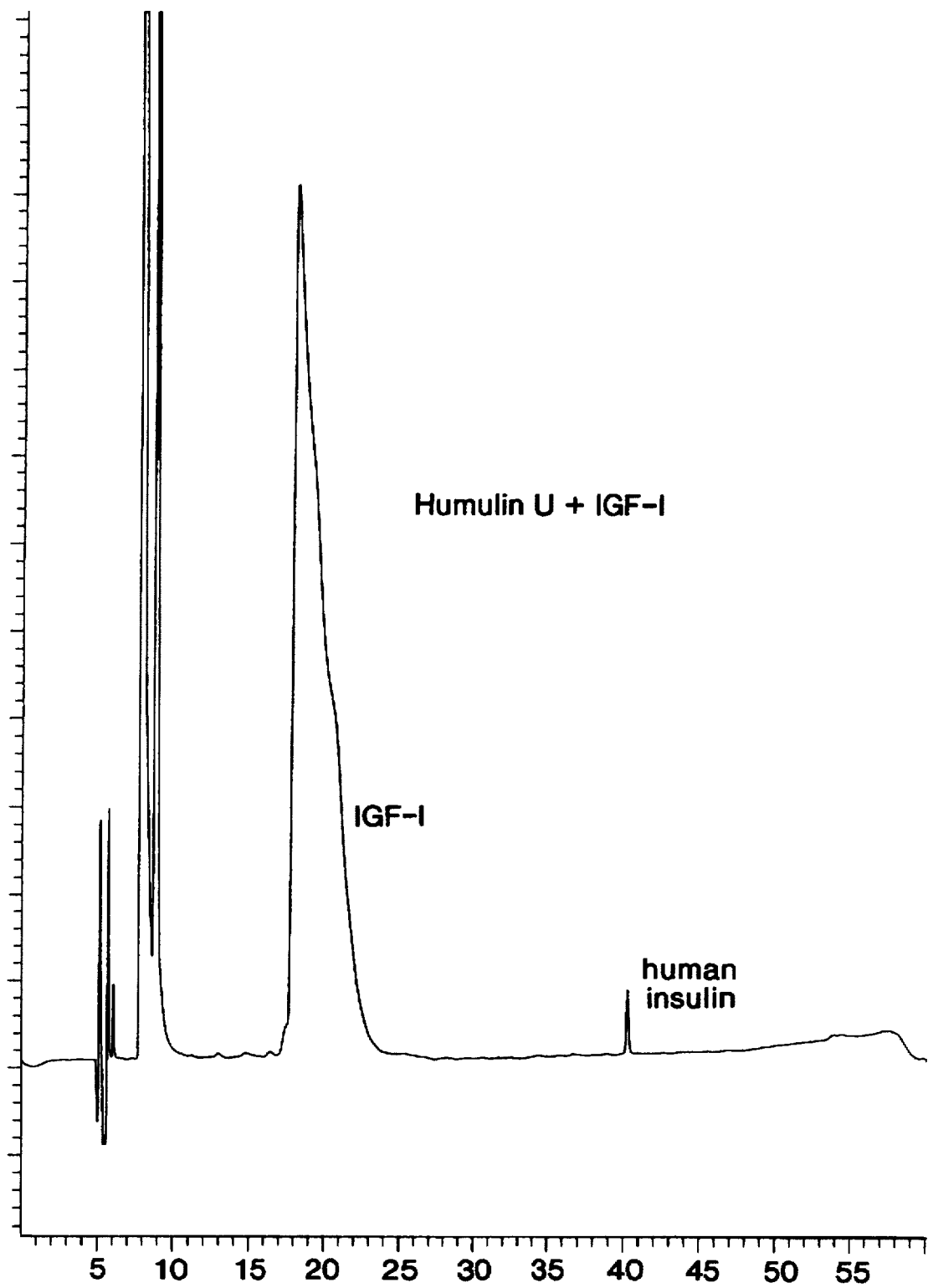
FIG. 3B depicts an acidic pH reversed-phase chromatogram of HUMULIN® U brand insulin plus IGF-I.

The size and shape of HUMULIN® U crystals did not seem to be affected by addition of IGF-I. FIG. 3A is an acidic pH reversed-phase chromatogram of HUMULIN® U. Since human insulin was present as crystals, human insulin was not detected in the solution by reversed-phase chromatography. FIG. 3B shows an acidic pH reversed-phase chromatogram of HUMULIN® U plus IGF-I. After addition of IGF-I, approximately 0.7% of total human insulin was released from the HUMULIN® U crystals. The peak shape of IGF-I has been slightly altered; however, the peak area of IGF-I was not affected.

HUMULIN® L and NOVOLIN® L (Lente)

Figure 4A:
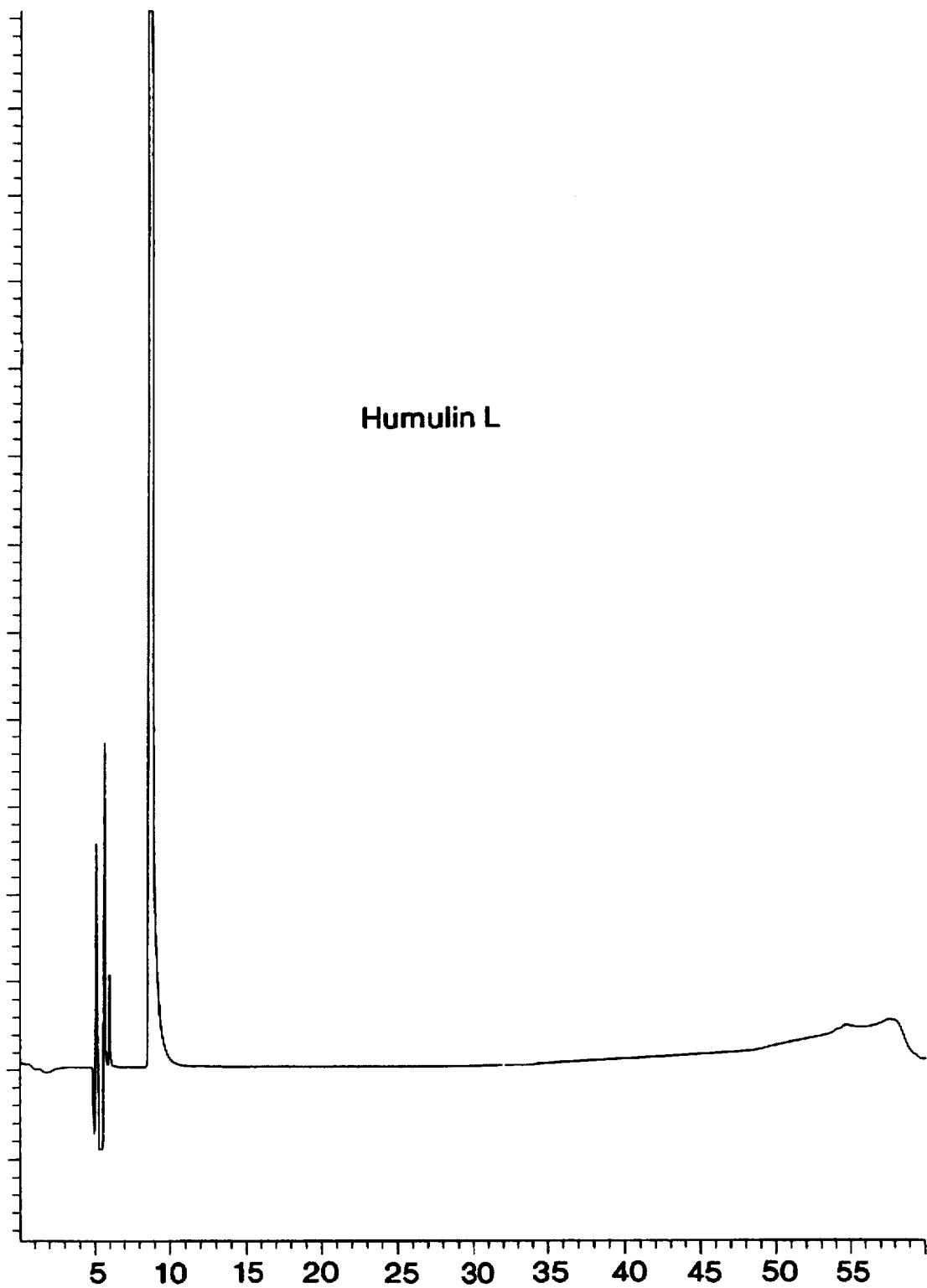
FIG. 4A depicts an acidic pH reversed-phase chromatogram of HUMULIN® L brand insulin without IGF-I.
Figure 4B:
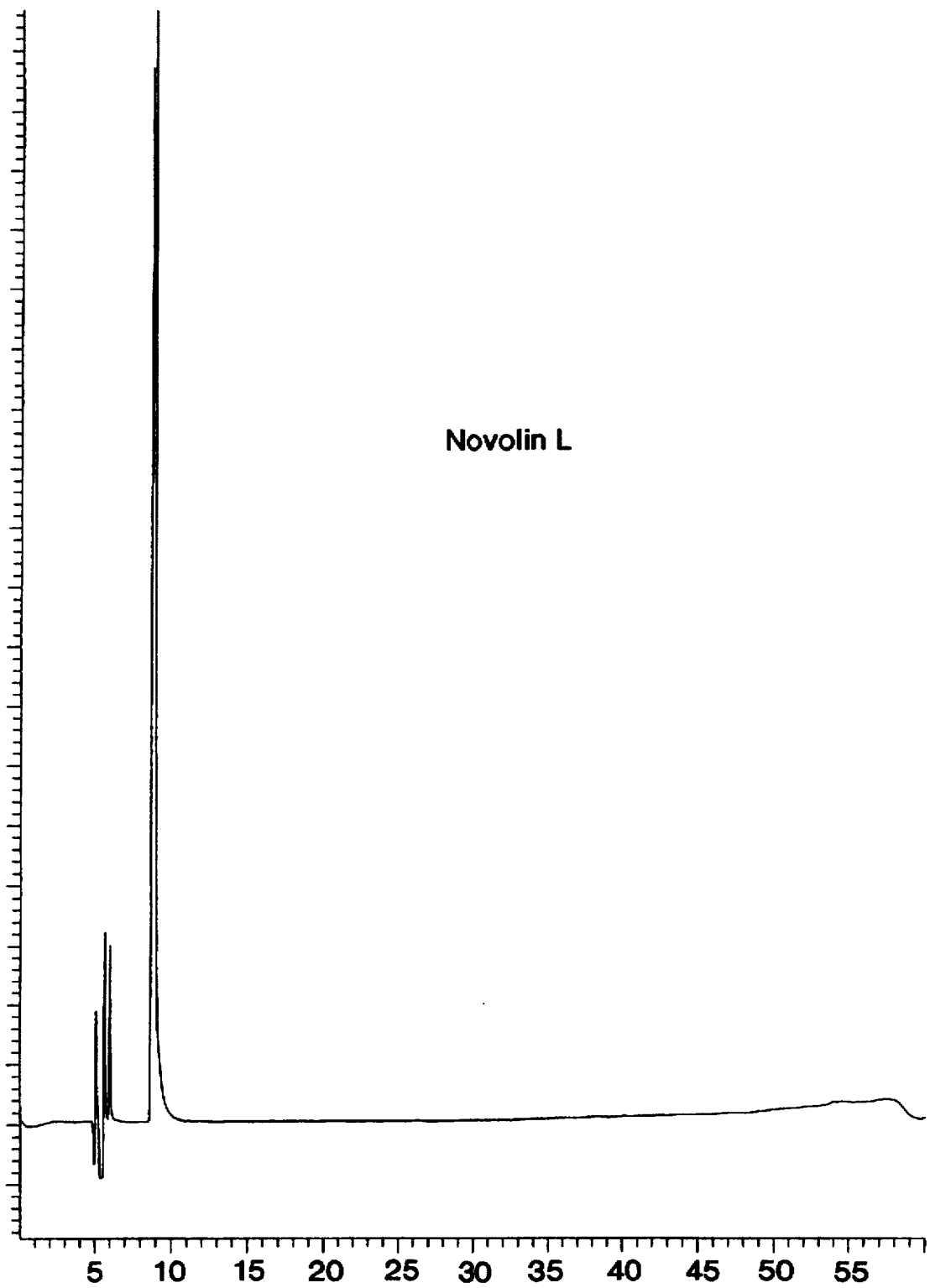
FIG. 4B depicts an acidic pH reversed-phase chromatogram of NOVOLIN® L brand insulin without IGF-I.
Figure 5A:
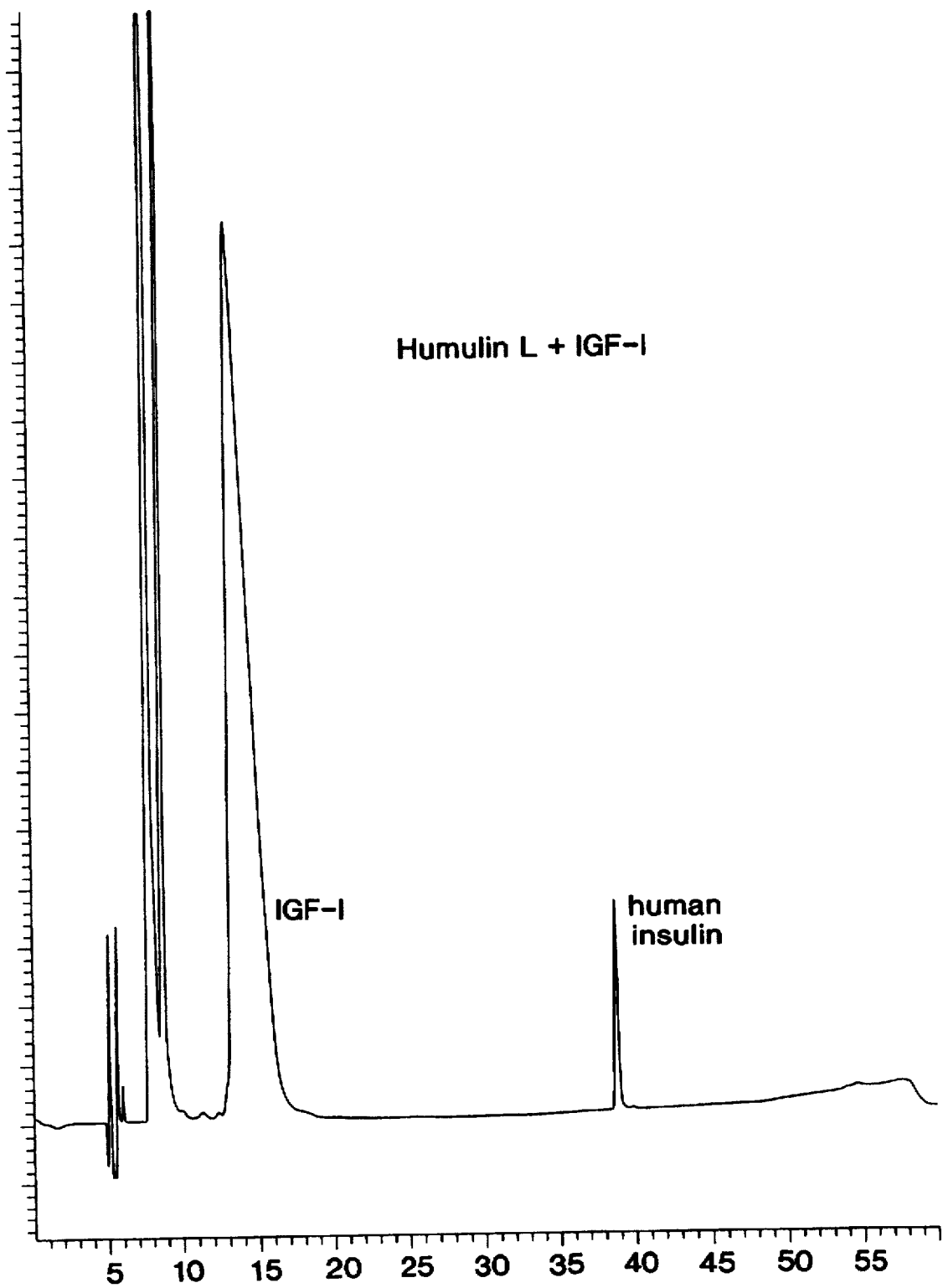
FIG. 5A depicts an acidic pH reversed-phase chromatogram of HUMULIN® L brand insulin with addition of IGF-I.
Figure 5B:
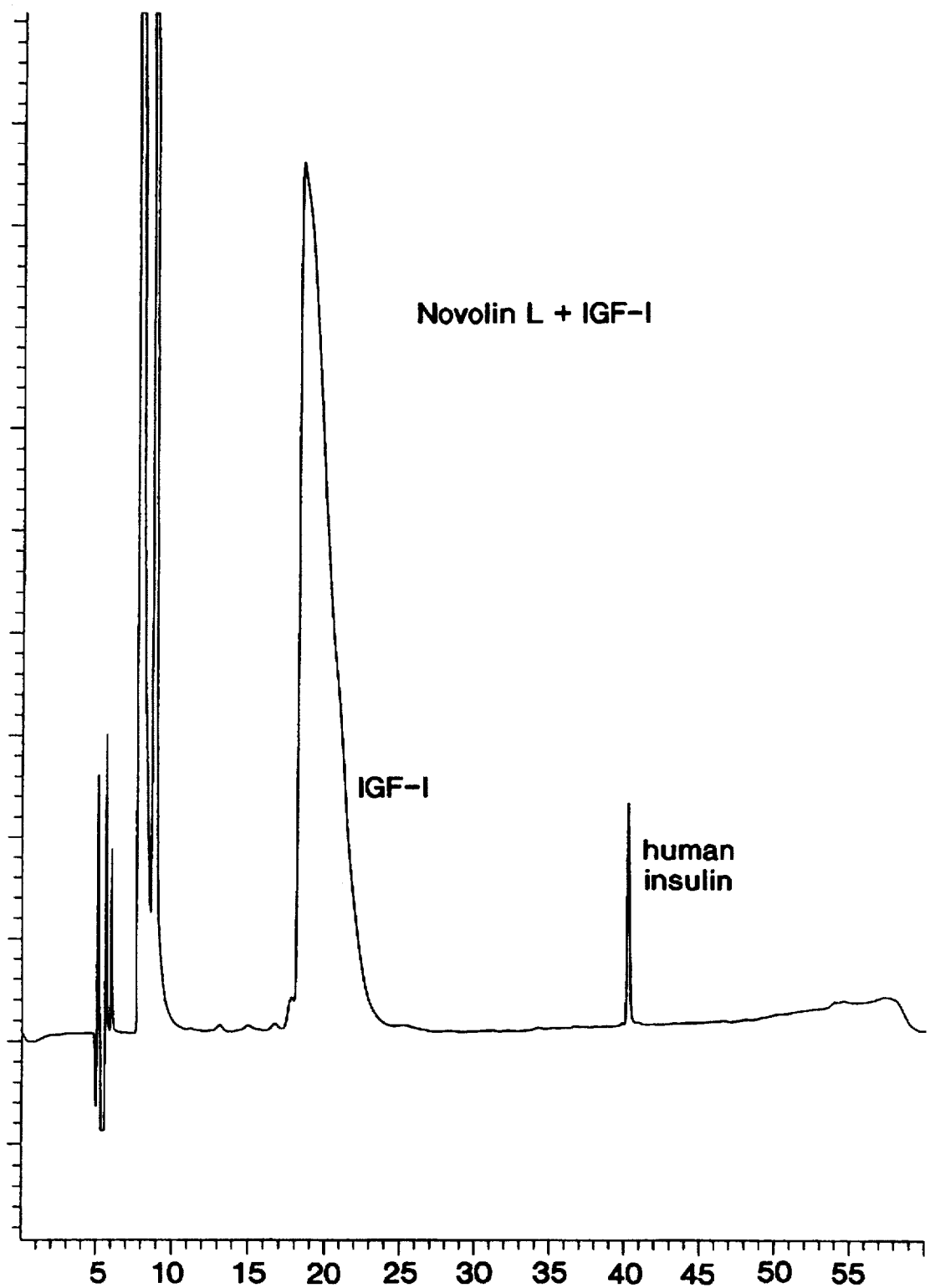
FIG. 5B depicts an acidic pH reversed-phase chromatogram of NOVOLIN® L brand insulin with addition of IGF-I.
Figure 7:
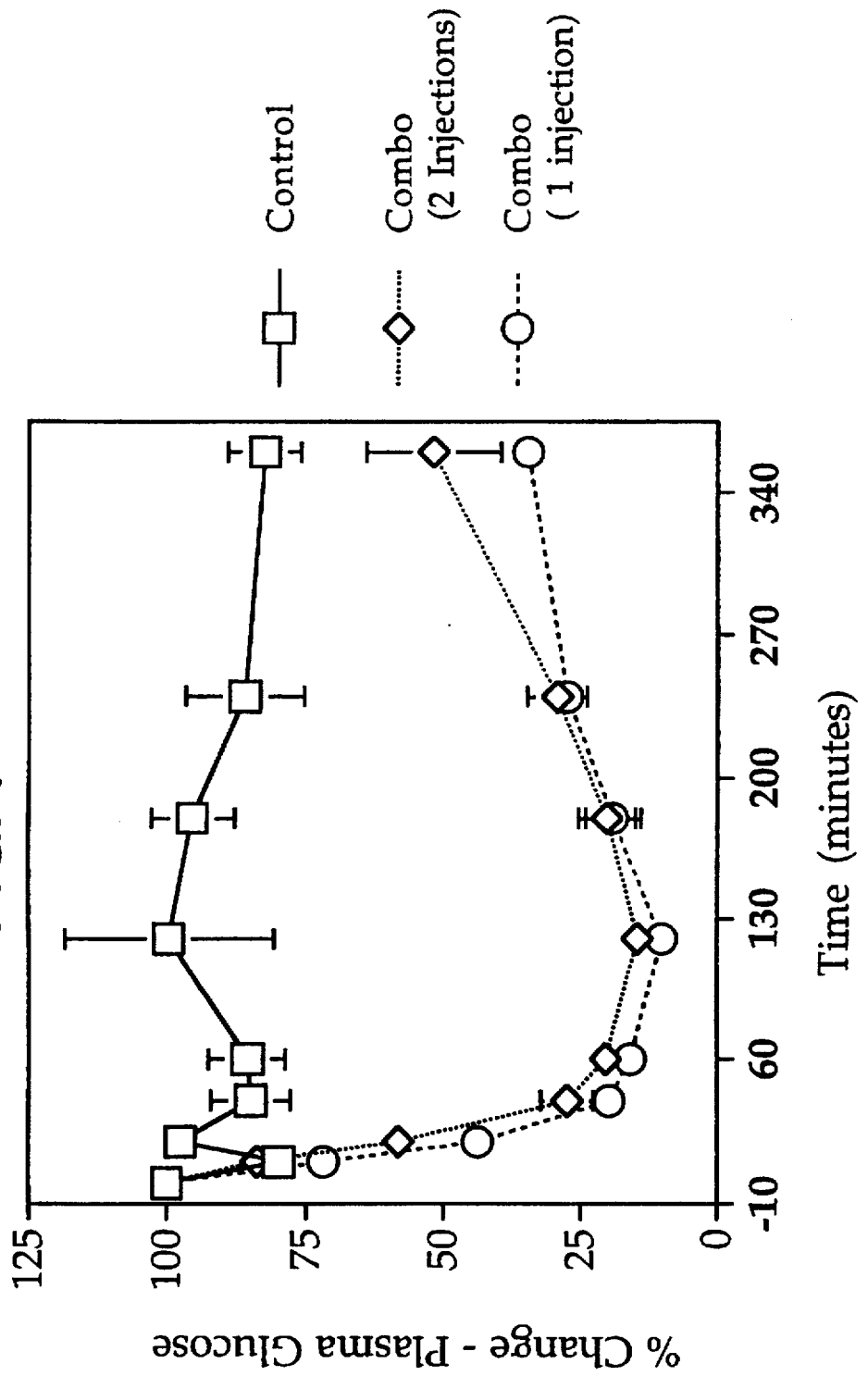
FIG. 7 shows a comparison of separate and single injections of IGF-I and NPH insulin SC in STZ diabetic rats, by depicting a graph of percent change in plasma glucose versus time for the control (open squares), two separate injections (open diamonds), and a single injection of IGF-I and NPH insulin (open circles).

HUMULIN® L is 30% amorphous and 70% crystalline human insulin. The size and shape of amorphous or crystalline human insulin appeared to be unchanged with the addition of IGF-I. FIGS. 4A and 4B show respectively the acidic pH reversed-phase chromatograms of HUMULIN® L and NOVOLIN® L without IGF-I. Human insulin presented as insoluble amorphous or crystalline form; therefore, it was removed by centrifugation and filtration. No human insulin was detected. FIGS. 5A and 5B show respectively the acidic pH reversed-phase chromatograms of HUMULIN® L and NOVOLIN® L with addition of IGF-I. After addition of IGF-I, approximately 4.8% of total human insulin was released into the solution. The peak area of IGF-I remained unchanged; however, the peak shape was slightly altered.

CONCLUSION

The data indicate that only HUMULIN® N and NOVOLIN® N are fully compatible with IGF-I.

EXAMPLE II

The purpose of these experiments was to determine the effects on blood glucose, plasma insulin, and plasma IGF-I concentrations of rhIGF-I and NPH insulin when injected in combination as subcutaneous (SC) injections to diabetic rats. In these experiments, recombinant human IGF-I and NPH insulin were given by SC injection either mixed together as one solution and given as one injection or given as two separate injections at two different sites.

PROCEDURE

| Streptozotocin (STZ) anesthesia (75 mg/kg) in citric acid buffer intraperitoneal (IP) | day 0 |
| --- | --- |
| cannulation of diabetic rats | day 5 |
| Study 1 | day 7 |
| Study 2 | day 9 |

METHODS

Animals/Surgery

Forty 7-8 week-old male SD rats were received from Charles River Laboratories and one day later injected with STZ 75 mg/kg IP. Five days later rats were bled via a tail vein, serum was obtained, and glucose concentration measured. All animals with blood glucose <200 mg/dL were not considered diabetic and were removed from the study. The remaining animals were then cannulated in the following manner: Rats were anesthetized (KETAMINETM™, 65 mg/kg, and XYLAZINETM™, 12.5 mg/kg IP) and a shaved surgical site was prepared using 70% isopropyl alcohol, then betadine solution. The right jugular vein was then isolated through a small SC incision and cannulated using a 0.02 inch×0.037 inch beveled silicon rubber-tipped cannula. Cannulas were flushed and checked for patency using heparin (10 U/mL) before closing wounds using 4-0 silk suture thread. Cannulas were "heparin locked" using ~50 µl heparin (100 U/mL) just before the animals were placed on a heated pad for recovery. Rats were placed in their vivarium cage when ambulatory.

The cannulas were flushed daily with fresh heparin/saline to maintain patency. Two days after cannulation, Study 1 (see below) was performed and two days later, Study 2. For these studies an extension tube of 12 inches of PE40 polyethylene tubing filled with heparin/saline was attached to the cannula after withdrawing the pin plugging the cannula. This line was connected to a syringe and left attached to the animal throughout the experiment. After each blood sample an equal volume of saline was re-injected via the cannula to maintain blood volume. Blood was sampled at the following times:

at −10 minutes, at 0 minutes, then the solutions shown below were injected, then blood was sampled again after 10, 20, 40, 60 minutes, 2, 3, 4, 6 hours.

In each study there were 4 or 5 rats per group. Data are Mean±SEM with comparisons by Duncan's Test. A statistically significant result was gauged if p<0.05.

Study 1

The experimental design was as follows:

| Group | | Concentration (µL) (SC) |
| --- | --- | --- |
| 1 | rhIGF-I placebo (pH 5.4 acetic acid formulation) | 50 |
| 2 | rhIGF-I.500 µg (from 10 mg/mL stock) | 50 |
| 3 | NPH insulin 5U (from 100 U/mL stock) | 50 |
| 4 | rhIGF-I + NPH insulin two separate injections | 50 × 2 |
| 5 | rhIGF-I + NPH insulin single injection | 100 |

Study 2

The experimental design was as follows:

| Group | | Concentration (µL) (SC) |
| --- | --- | --- |
| 1 | rhIGF-I placebo (pH 5.4 acetic acid) | 50 |
| 2 | rhIGF-I + NPH insulin two separate injections | 100 × 2 |
| 3 | rhIGF-I + NPH insulin single injection | 100 |

Compounds used 1) rhIGF-I (Genentech Inc, lot #G117AZ/A9841AX) 10 mg/mL diluted 1:2 with IGF-I placebo. The rhIGF-I consists of 10 mg/mL IGF-I, 5.84 mg/mL NaCl, 9.0 mg/mL benzyl alcohol, 2.0 mg/mL polysorbate 20, 50 mM sodium acetate, pH 5.4. The intended final product configuration contains 7 mL (70 mg) of the above solution in a 10-mL glass vial, which is generally stored refrigerated (2°–8° C.) to maximize its lifetime. This product is designed to be a ready-to-use liquid for subcutaneous or intravenous administration using a conventional needle and syringe.

2) IGF-I placebo (sodium acetate buffer at pH 5.4)=5 mg/mL:100 µL=500 µg

3) NPH insulin (HUMULIN® N, Eli Lilly, Lot #9MF78M) 100 U/mL diluted 1:2 with sterile water=50 U/mL:100 µL=5 U 4) Sterile Water Measurements Plasma glucose concentrations were measured using a Chem 1A serum chemistry analyzer (Miles Laboratories, Tarrytown, N.Y.). Insulin in plasma was measured by rat-specific radioimmunoassay (RIA) (Linco Research Inc., St. Charles, Mo.). Plasma IGF-I was measured by RIA after acid-ethanol extraction of the samples.

RESULTS

Study 1

The diabetic state of the rats is shown (FIG. 6) by the blood glucose levels (400 mg/100 mL) in the animals. Compared to the control group, which was injected with excipient, all treatments caused a significant fall in plasma glucose levels. There was a clear difference between the groups in the initial glucose response. The single-injection combination group (treated with IGF-I+NPH insulin) had a substantially lower plasma glucose level 10 and 20 min. after injection than all the other groups. Twenty minutes post-injection the blood glucose levels were: Placebo 409.5±66.5; rhIGF-I 218.3±38.1; NPH insulin 240.3±24.1; two separate injections 240.3±61.3; single injection 151.0±17.9 mg %. Blood glucose levels in the IGF-I-treated rats returned to basal values after 6 hours, but in the rats given NPH insulin alone, or given the mixture of NPH insulin and IGF-I, blood glucose levels remained significantly depressed even after 6 hours.

Study 2

In the second study the dosing volume was adjusted to test if concentration and injection volume might be factors in the difference seen between the one-injection and two-injection combination groups in Study 1. Therefore, in the two-injection combination group, animals received 100 µl each of NPH insulin and rhIGF-I (half the concentration and twice the volume but equivalent dose of Study 1). In the single-injection group, 100 µL of solution was injected which contained both IGF-I and NPH insulin. This study was similar to Study 1 in all other respects.

All treatments caused a significant fall in plasma glucose levels. However, the single-injection group substantially decreased plasma glucose levels even after only 10 minutes (placebo 380±21.3; two separate injections 388±13.3; single injection 332±14.8 mg %): and 20 minutes after the injection (placebo 445.3±17.6; two separate injections 275.4±25.3; single injection 216.8±19.5 mg %). This decrease was also noted on a relative percent change basis. Therefore, it did not appear that the injection volume or the concentration were the cause of the difference between the separate-injection and the single-injection groups.

Insulin and IGF-I Levels in Blood

To understand why the co-injection of the combination of IGF-I and NPH insulin gave a more rapid onset of hypoglycemia, the insulin and the IGF-I concentrations in blood were measured.

Figure 8:
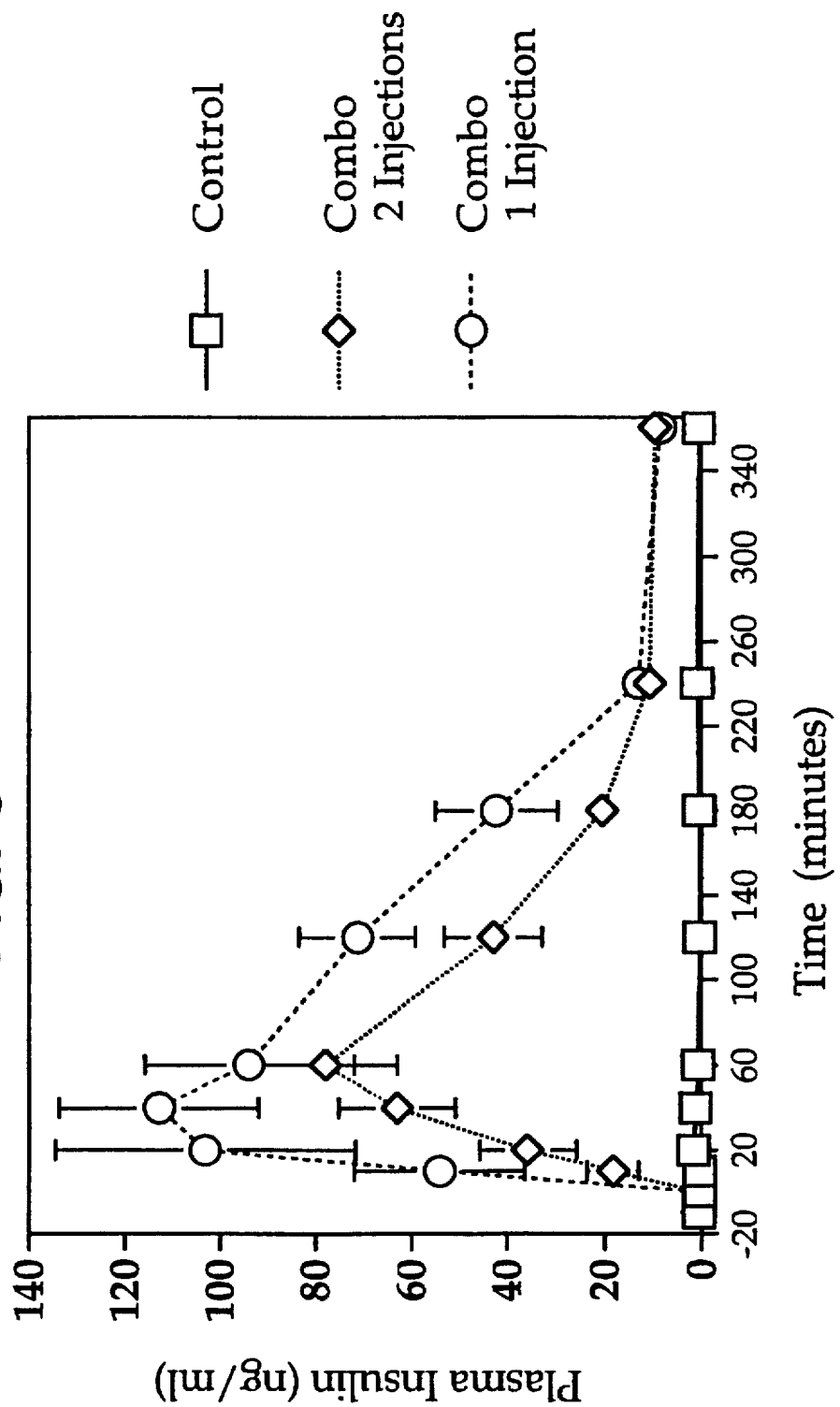
FIG. 8 shows a comparison of separate and single injections of IGF-I and NPH insulin SC in STZ diabetic rats, by depicting a graph of plasma insulin versus time for the control (open squares), two separate injections (open diamonds), and a single injection of IGF-I and NPH insulin (open circles).
Figure 9:
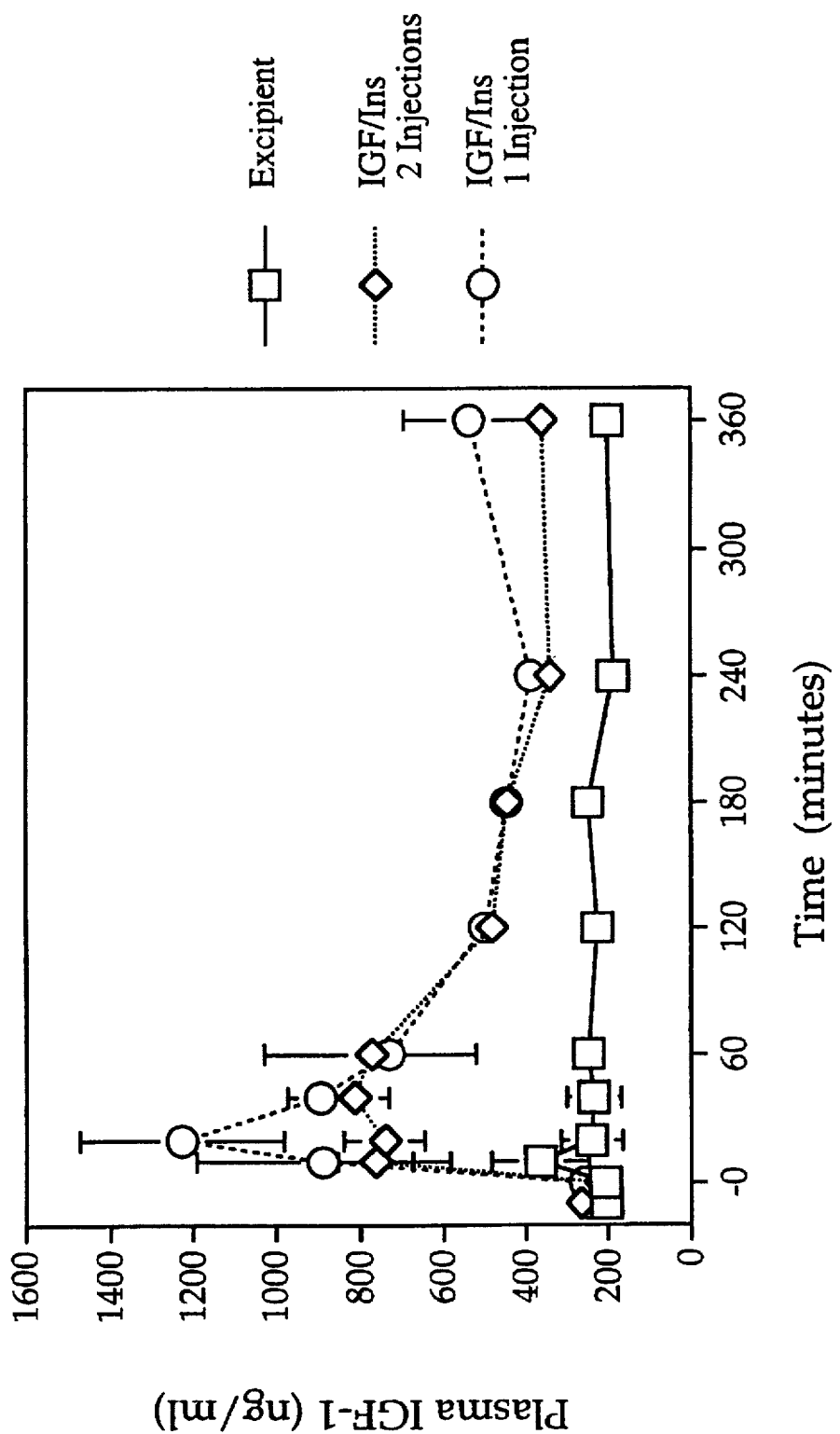
FIG. 9 shows a comparison of separate and single injections of IGF-I and NPH insulin SC in STZ diabetic rats, by depicting a graph of plasma IGF-I versus time for the excipient (open squares), two separate injections (open diamonds), and a single injection of IGF-I and NPH insulin (open circles).

FIG. 8 shows that there was a significant treatment effect on plasma insulin. At forty minutes post-dosing the single-injection combination increased plasma insulin almost two-fold compared to the separate-injection group (placebo 1.15±0.45, two separate injections 63.0±12.2, single injection 112.8±21.0 ng/mL; p<0.05 vs. two separate injections). FIG. 9 shows the serum IGF-I concentrations after the co-delivery of IGF-I and NPH insulin, or after their separate injection. Serum IGF-I concentrations were significantly higher in the single-injection combination treatment group than in the separate-injection group at 20 min. post-injection. Therefore, the co-formulation of NPH insulin and IGF-I gave greater efficacy than if the formulations were injected separately and this increased efficacy was associated with a more rapid appearance of insulin in the blood and possibly of IGF-I in the blood.

Study 1 and 2 Combined Glucose Data

When glucose data are combined, a significant difference was seen in treatment regimen at 10 and 20 min. post-injection. The single-injection treatment caused a more rapid decrease in plasma glucose which was statistically significant 10 minutes post-injection (placebo 365.7±18.6 mg/dL, two separate injections 368.7±17.3 mg/dL, single injection 311.8±12.4 mg/dL).

Study 3

This experiment in diabetic rats was designed to discover:
1) If the IGF-I placebo itself affected the efficacy and absorption of NPH insulin.
2) If at doses of NPH insulin and IGF-I other than those used in Studies 1 and 2 effects of co-delivery could be seen.

The experimental design was as follows:

| Group | | Concentration (µL) (SC) |
|---|---|---|
| 1 | NPH insulin 2.5 U 1:1 in sterile water | 50 |
| 2 | NPH insulin 2.5 U 1:1 in IGF-I placebo | 50 |
| 3 | NPH insulin 2.5 U + IGF-I 250 µg single injection | 100 |
| 4 | NPH insulin 2.5 U + IGF-I 250 µg two separate injections | 100 × 2 |

All methods and procedures were identical to those used in Studies 1 and 2.

Figure 10:
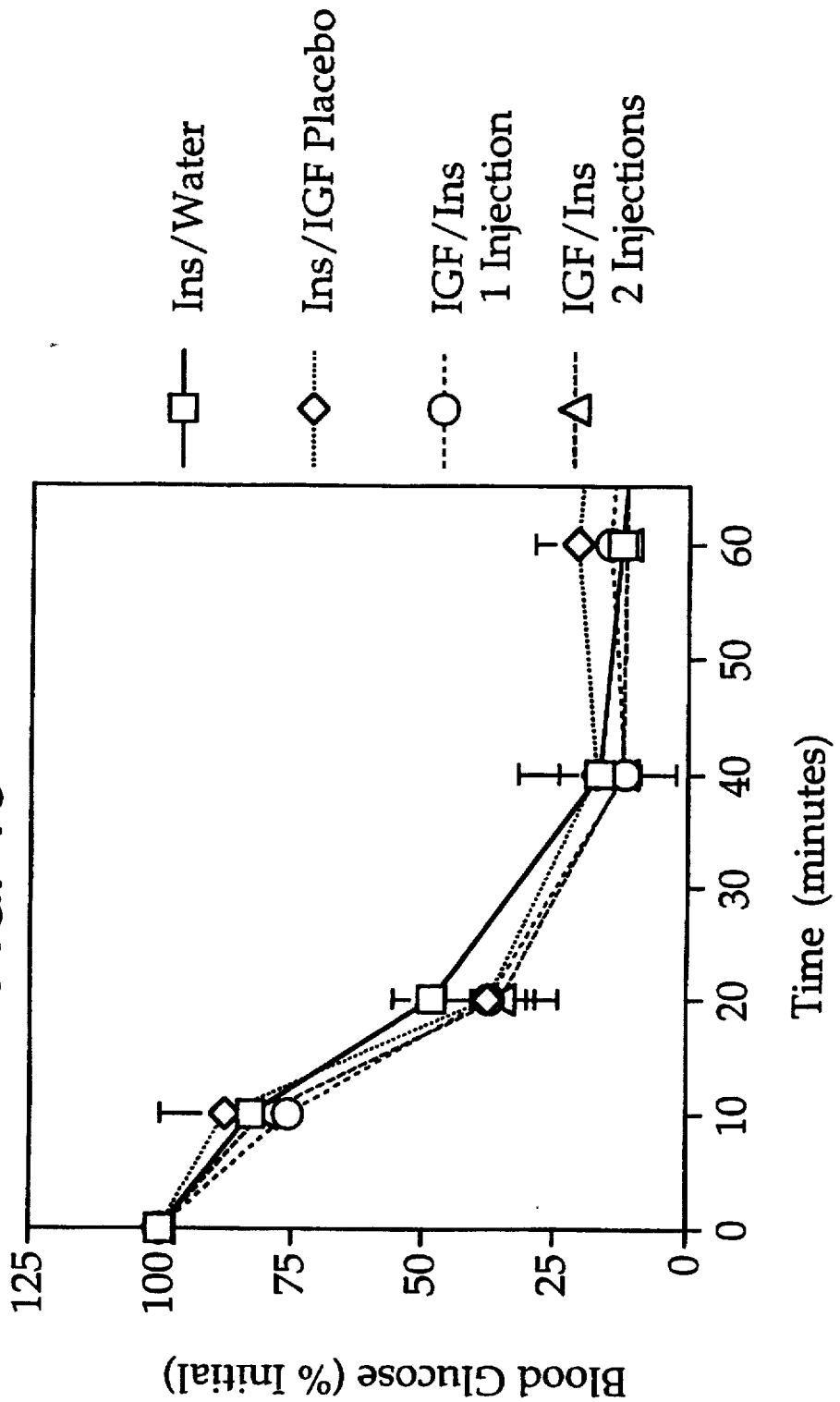
FIG. 10 shows a comparison of various SC injections in STZ diabetic rats, by depicting blood glucose versus time for NPH insulin in water (open squares), NPH insulin in IGF-I placebo (open diamonds), a single injection of IGF-I and NPH insulin (open circles), and two separate injections of IGF-I and NPH insulin (open triangles).

The blood glucose data, expressed as percentage of control, for the first hour post-injection from this study are shown in FIG. 10. It can be seen that mixing the NPH insulin in the IGF-I buffer (group 2) tended to give a greater effect on blood glucose than mixing the NPH insulin into water (group 1). This suggests a direct effect of the IGF-I buffer on the absorption of NPH insulin.

Figure 11:
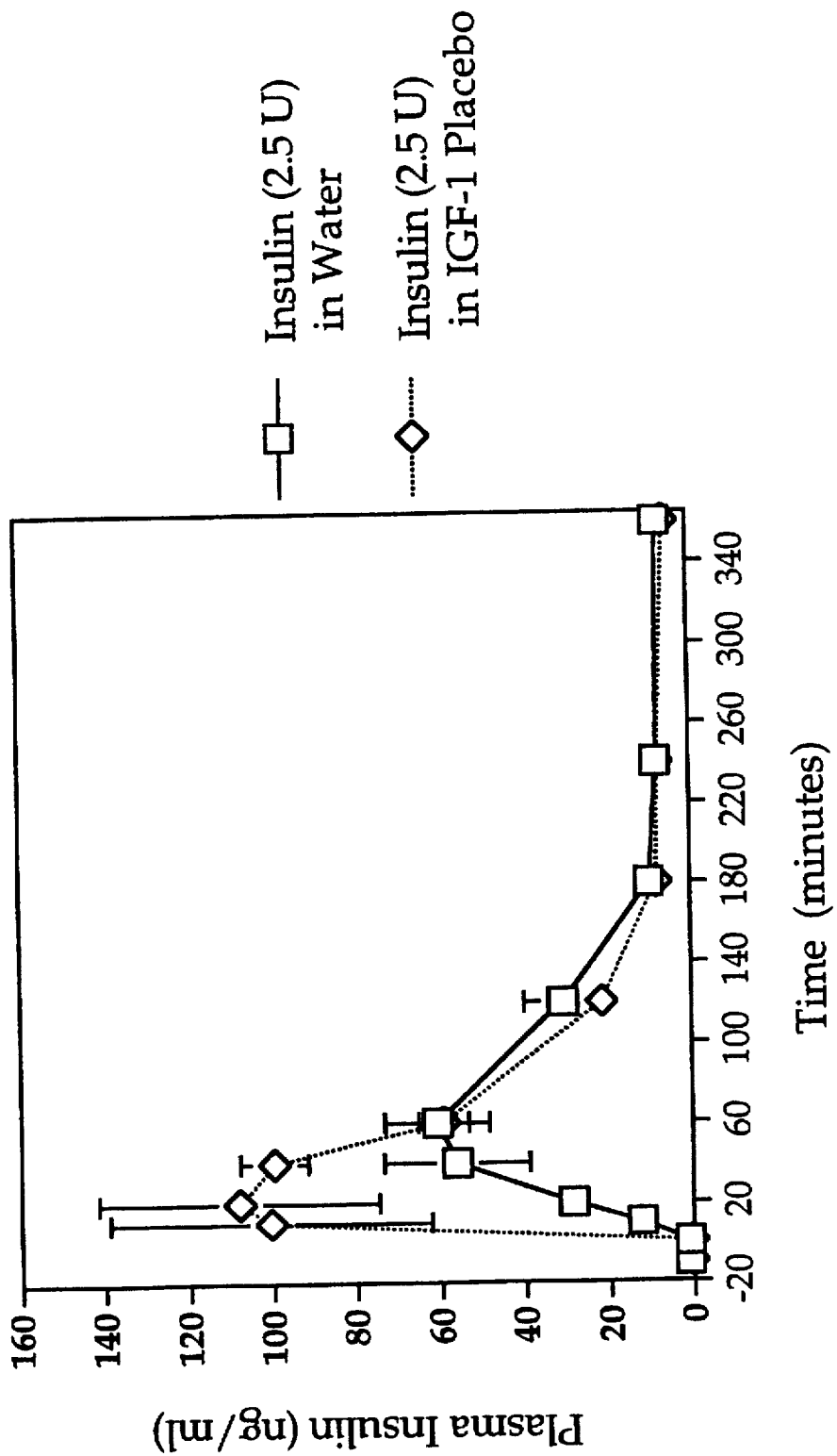
FIG. 11 shows the effect of IGF-I placebo on blood insulin in STZ diabetic rats injected SC, by depicting plasma insulin versus time for NPH insulin in water (open squares) and NPH insulin in IGF-I placebo (open diamonds).
Figure 12:
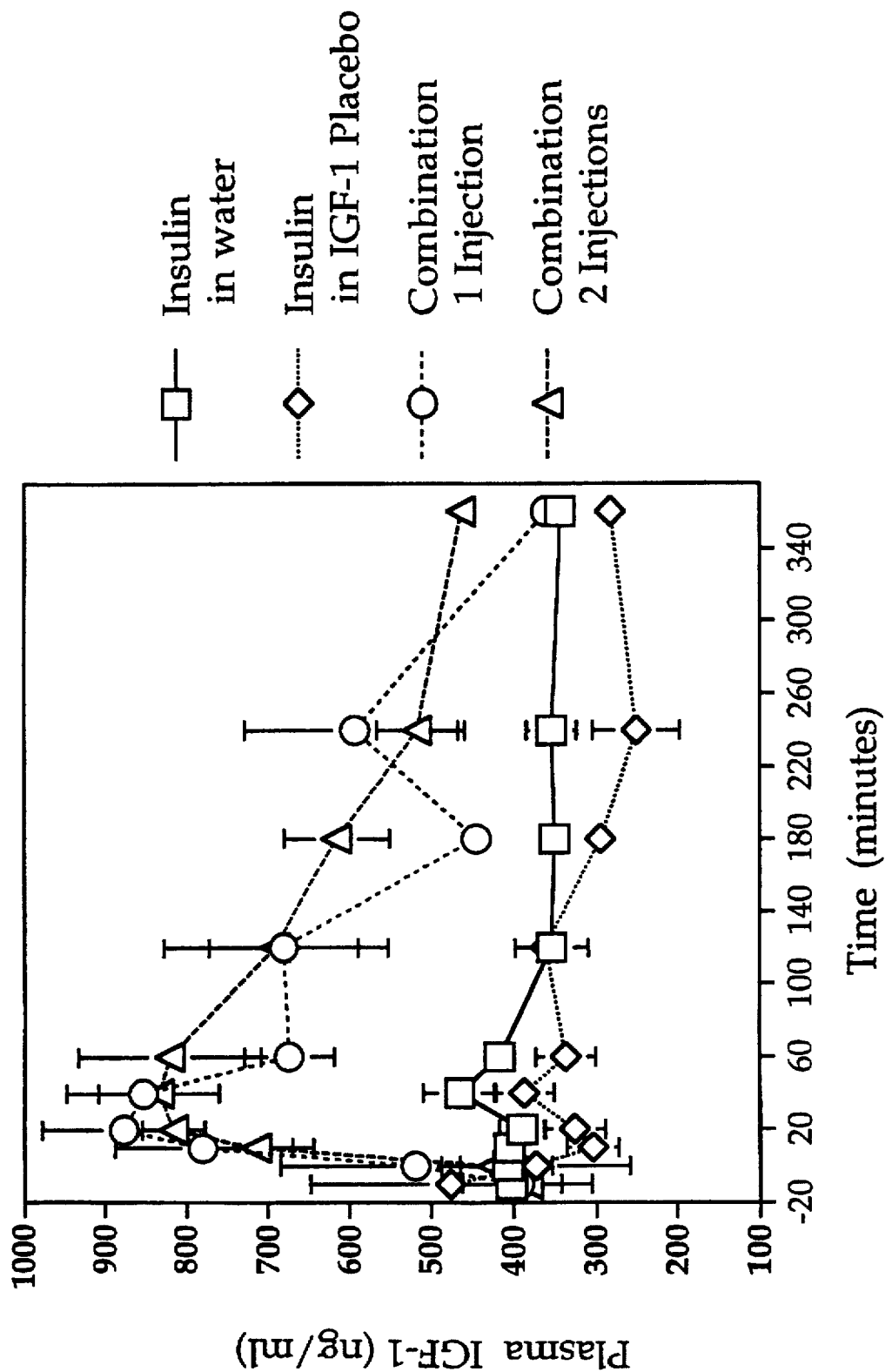
FIG. 12 shows a comparison of various SC injections in STZ diabetic rats, by depicting plasma IGF-I versus time for NPH insulin in water (open squares), NPH insulin in IGF-I placebo (open diamonds), a single injection of IGF-I and NPH insulin (open circles), and two separate injections of IGF-I and NPH insulin (open triangles).

Measurement of insulin (FIG. 11) confirmed that diluting the NPH insulin in the IGF-I placebo, rather than with water, increased insulin absorption. A comparison of FIGS. 8 and 11 shows that the effect on insulin absorption of co-mixing NPH insulin and IGF-I (FIG. 8) can be duplicated by adding the formulation buffer for IGF-I to the NPH insulin. Without being limited to any one theory, it is believed that the more rapid absorption of insulin shown in FIG. 8 is probably not due to the presence of IGF-I but is due to the formulation buffer used to dissolve the IGF-I. Measurement of the IGF-I concentrations (FIG. 12) in this experiment showed that the absorption of IGF-I was unaffected by being co-mixed with NPH insulin.

In conclusion, at these lower doses of NPH insulin and IGF-I the effects seen on insulin absorption in Studies 1 and 2 were duplicated in Study 3. In addition, it was found that IGF-I itself was not essential for the increased absorption of insulin; the IGF-I placebo by itself caused a more rapid increase in blood insulin concentrations.

SUMMARY

These studies show that the co-formulation of NPH insulin and IGF-I leads to unexpectedly lower glucose levels. This is an advantage in the management of diabetic patients, because the number of injections the patients must self-administer would be reduced. The only means by which it is possible to co-inject IGF-I and insulin is by using NPH insulin. The preferred method of delivery is using an IGF-I acetate-buffered formulation, as this formulation allows a more rapid absorption of the NPH insulin. This more rapid absorption of insulin has advantages over current methods of insulin administration.

NPH insulin is a relatively long-acting form of insulin that is usually given in the evening to maintain insulin concentrations overnight. Before the evening meal it is usual in addition to give an injection of a short-acting insulin. The current invention discloses an advantage in that a rapid release of a portion of the insulin occurs if NPH insulin is given with IGF-I. Therefore, for example, instead of a diabetic patient being given two injections, NPH insulin at bedtime and regular insulin before dinner, the current invention allows one injection of IGF-I/NPH insulin to be given before dinner. A reduction of the number of injections is therefore achieved.

Hence, it is evident that there are multiple benefits of this invention. These benefits include the use of a fewer number of injections of insulin and rhIGF-I, the use of fewer insulin injections, and an altered pharmacokinetics of NPH insulin.

EXAMPLE III

There do not appear to be any well-controlled clinical trials assessing the longer-term effects of rhIGF-I/insulin combination therapy in the sub-population of IDDM patients. Therefore, to investigate whether such a dual hormonal replacement paradigm may be superior to insulin mono-therapy, a four-week, randomized, placebo-controlled, double-blind study was conducted. Glycemic control during rhIGF-I plus insulin was compared and contrasted with a group treated with insulin as sole therapy. The subjects were both children and adolescents with IDDM. This study, while not giving to the patients the formulation containing IGF-I and insulin as now claimed, but rather separate injections, indicates the dosing that would be typical in a clinical setting for this indication.

METHODS

Forty-three patients (22 males and 21 females) with IDDM, ages 8–17 years, were recruited at three university-based diabetes clinics. The eligibility criteria were as follows:

1. Age equal to or older than 8 years.
2. IDDM duration $\geq 6$ months.
3. suboptimal metabolic control, defined by glycosylated hemoglobin ($HbA_1$) equal to or over the mean $HbA_1$ for IDDM patients seen at that clinic. This is determined by each site's laboratory (Duke and Philadelphia $HbA_{1c} \geq 8.4\%$ and 8.2%, respectively; Buffalo $HbA_1 \geq 10.4$) on a minimum of two occasions within 4 months prior to study entry.
4. a twice-a-day injection regimen of regular and NPH insulin for at least 6 months. Associated medical conditions (except for autoimmune thyroiditis on replacement therapy), biochemical and/or clinical evidence of diabetes complications, and use of medications other than insulin or L-thyroxine were exclusion criteria. Also excluded were patients with previous history of a psychiatric disorder, ethanol abuse, cancer, or recent use (within 30 days of study entry) of other experimental agents/procedures. The study was approved by the Institutional Review Board of each institution. The subjects and/or one of the parents provided signed informed consent.

Study Design

Figure 13:
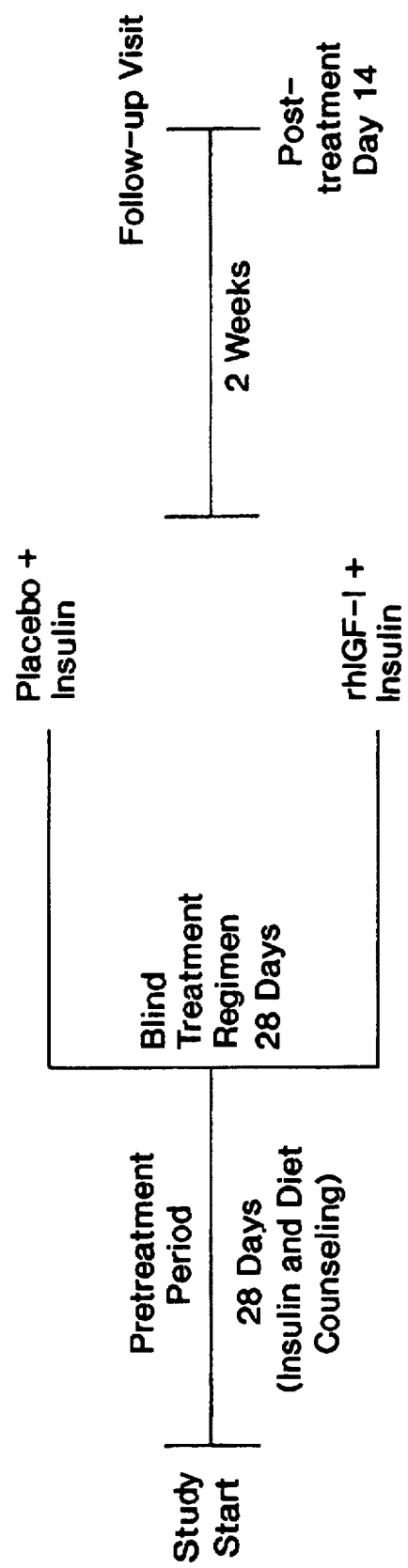
FIG. 13 shows a clinical study design involving four weeks of outpatient diabetes counseling followed by four weeks of treatment of patients having IDDM with insulin and either rhIGF-I or placebo. The study ended with a two-week period of wash-out.

The study design included a 4-week lead-in period, a 4-week treatment period, and a 2-week wash-out period (FIG. 13). Throughout the study the patients continued to receive two injections of regular and NPH insulin daily. At study entry the patients were provided with detailed instructions on home blood glucose (BG) monitoring technique. They were instructed to test BG before breakfast, lunch, dinner, and the evening snack as well as any times of symptomatic hypoglycemia. The glucose values were automatically stored in the meter (One Touch II—Lifescan Inc., Milpitas, Calif.) and electronically transferred to a personal computer at the study site during each clinic visit. During the lead-in period the patients were counseled weekly on general diabetes care and dietary management (day −28 and −14 at the clinic, day −21 and −7 over the phone). During this period the patients were provided with specific goals of glycemic control and were instructed to call the study sites as often as needed for assistance with insulin adjustment.

At the end of the lead-in period the patients were randomized to administer either rhIGF-I or placebo as an additional injection immediately before their morning insulin injections. Patients were allocated using an adaptive randomization procedure that stratified based on Tanner stage and the glycosylated hemoglobin value on day −28 of the lead-in period. A seven-day window period was allowed between day −1 of the lead-in period and day 1 of the treatment period. The subjects were admitted to the hospital the afternoon preceding day 1 of treatment and received their usual insulin dose and diet. On day 1, an IV cannula was inserted into the distal forearm or antecubital fossa. A single dose of rhIGF-I (80 µg/kg) or placebo was administered SC, followed by a SC insulin injection and breakfast. The dosing of IGF-I in the morning was for safety reasons. On day 1, the a.m. regular insulin dose was reduced by ½ in both groups as a precaution against the development of hypoglycemia. Blood samples were obtained for future assay every 15 minutes for the next 3 hours. The patients were encouraged to be active and exercise after the initial 3-hour sampling period. Discharge from the hospital occurred on day 3 or 4 of treatment. The patients were then contacted by phone on day 5 and seen as outpatients on days 7, 14, 21, and 28 of treatment and 14 days after the cessation of dosing. The patients were instructed on dietary and diabetes management at each follow-up appointment.

For the entire four-week treatment period, the rhIGF-I and placebo doses remained constant (80 µg/kg SC q a.m.). However, the insulin doses were adjusted in an attempt to achieve the following BG targets: fasting blood glucose (FBG) 80–120 mg/dl (4.4–6.7 mmol/L) for age greater than 12 years and 80–140 mg/dL (4.4–7.8 mmol/L) for age lower than 12 years; 80–180 mg/dL (4.4–10.0 mmol/L) at any other time. A physical exam was performed on day −28 of the lead-in period, on days 1, 7, 21 and 28 of the treatment period, and on day 14 of the wash-out period. The treatment period was followed by a two-week wash-out period, during which the patients remained on insulin therapy only and dose adjustments continued as necessary to meet the glycemic goals.

Laboratory Evaluations

Table II summarizes the laboratory evaluations carried out during the study.

TABLE II

| | Study Flow Chart | | | | | | |
|---|---|---|---|---|---|---|---|
| | Lead-in | Treatment | | | | | Post-Treatment |
| Day | 1 | 1 | 7 | 14 | 21 | 28 | 14 |
| Medical history | | | | | | | |
| Physical examination | X | X | | | | X | X |
| Pregnancy test | X | X | | | | X | |
| CBC | X | X | | | | X | X |
| Chemistries | X | X | X | X | | X | X |
| Glycosylated hemoglobin | X | X | | X | | X | X |

TABLE II-continued

Study Flow Chart

| | Lead-in | Treatment | | | | | Post-Treatment |
|---|---|---|---|---|---|---|---|
| Day | 1 | 1 | 7 | 14 | 21 | 28 | 14 |
| HDL Cholesterol | X | X | | X | | X | X |
| GH, IGFs, and Bps | X | X | X | X | X | X | X |
| Free T4 and TSH | | X | | | | | |
| Urinalysis | X | X | | | | X | |
| Creatinine clearance/and 24-hour protein | | X | | | | X | |

Indices of glycemic control

The primary indices of glycemic control were: 1) $HbA_1$ was measured at day −28 of the lead-in, as well as at days 1 and 28 of the treatment; 2) the average of the four daily home glucose monitoring values over the last ten days of the lead-in period was compared to the last ten days of treatment. The glycosylated hemoglobin was assayed by affinity chromatography (SmithKline Beecham Clinical Laboratories). The reference range was 4.4–6.1%.

Growth hormone/IGF-I axis

Plasma levels of GH, IGF-I, free IGF-I, IGF-II, IGFBP-1, IGFBP-2, and IGFBP-3 were measured. Plasma IGF-I levels were obtained before and every 30 minutes for three hours following study drug administration on day 1 of treatment and 2–4 hours following study drug administration on days 7, 14, 21, and 28 of treatment. Total plasma IGF-I concentrations were determined by radioimmunoassay (RIA) following acid-ethanol extraction as described by Lieberman et al., supra. Free IGF-I in plasma was separated from IGF-I complexed to binding protein using size-exclusion HPLC (SE-HPLC) with a TSK G2000SW column and a mobile phase of 0.2M sodium phosphate, 0.5% Tween-20 at pH 6.5. Measurement of IGF-I levels after chromatography reveals IGF-I concentrations (extraction+RIA) of 7.0% and 19%. Free IGF-I concentration (SE-HPLC+RIA) has an inter-assay coefficient of variation of 17% at 100 ng/mL. Lieberman et al., supra.

Safety laboratory measures

The primary safety laboratory evaluations were serum biochemical and thyroid profiles, CBC, urinalysis, 24-hour urinary albumin excretion rate and creatinine clearance. Hypoglycemia was defined by a BG level equal to or lower than 50 mg/dL with or without symptomatology. This definition of hypoglycemia was used for purposes of statistical analysis.

Subject Discontinuations

According to the protocol, a patient was to be discontinued from the study if he or she missed five or more injections or 14 or more BG measurements throughout the study.

Statistical methods

Patients with at least two weeks of post randomization data were included in the analysis. For patients who discontinued early, but had at least two weeks of data for the treatment period, the last available data value was carried forward to day 28 and used in the analysis. The data are summarized by mean±SE for each group. Comparisons between the two groups were performed using the Wilcoxon rank sum test for continuous variables and Fisher's exact test for discrete data. All tests were two-tailed and a p-value less than or equal to 0.05 was considered statistically significant.

RESULTS

Baseline characteristics

As shown in Table III, baseline demographic characteristics of subjects in the rhIGF-I and placebo groups were similar. Four out of 21 subjects in the placebo and 4 of 22 in the rhIGF-I group were prepubertal.

TABLE III

Baseline Characteristics of Patients

| | rhIGF-I | Placebo |
|---|---|---|
| Male/Female | 14/8 | 8/13 |
| Age (yrs) | 12.6 (8–17) | 13.0 (9–16) |
| $HbA_1$ (%) | 11.3 (8.1–14.9) | 11.4 (9.9–16.4) |
| IDDM Duration (mos) | 66 (14–167) | 77 (13–192) |
| Weight (kg) | 51.8 (28.1–77.4) | 53.8 (31.9–89.8) |

Disposition of patients

Four patients terminated early from the study. One discontinuation occurred in the placebo group in response to the patient's request on day 6 of treatment. Three subjects underwent early discontinuation in the rhIGF-I group: one patient developed an episode of syncope, not associated with hypoglycemia, four hours after the study drug administration on day 1 of treatment. The patient was on antibiotic therapy for recurrent otitis media, but it is uncertain whether this was related to the event. The second patient had erratic BG levels in the lead-in period, with improvement during the treatment period; however, the subject experienced significant hypoglycemia which could not be adequately compensated by decreasing the regular insulin dose. The third patient was discontinued at the end of the lead-in period due to non-compliance with BG monitoring.

Glycemic control

Figure 14:
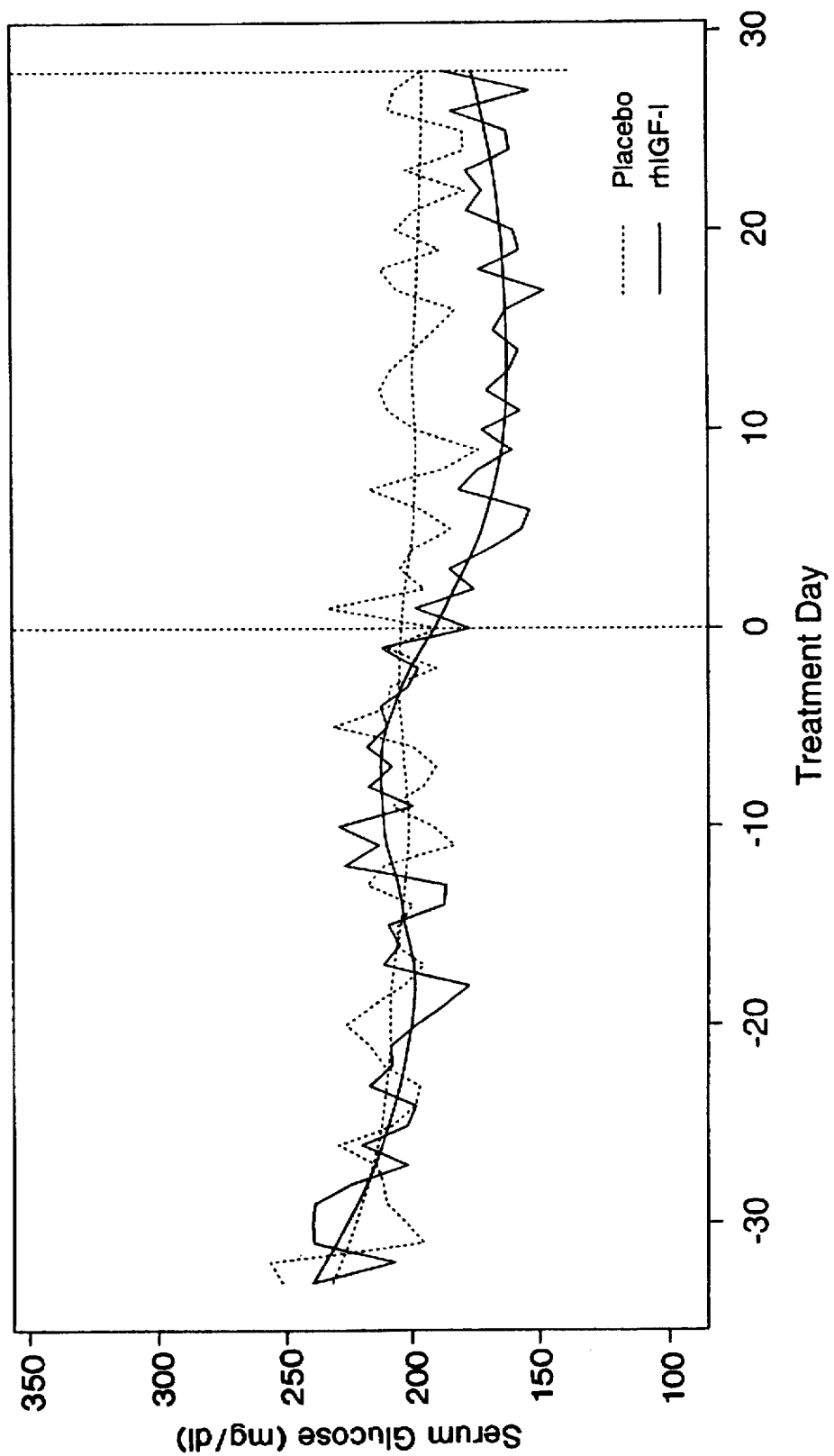
FIG. 14 shows the average daily glycemic levels and regression curve for the study shown in FIG. 13. The spiked and smooth lines represent the average of the four daily glucose levels and the best-fit regression curve, respectively. The regression curve lines, overlapping in the two groups during the pre-treatment period (day −30 to 0), separate during the treatment period (day 0 to 30), with a definite lowering of the regression line of the rhIGF-I-treated group vs. control. For S.I. unit conversion a multiplication factor of 0.05551 is employed.

The average daily BG levels during the last ten days of lead-in period (day −19 to −28) compared to the average BG values during the last ten days of treatment (day 19 to 28) are shown in Table IV. The overall improvement in glycemic control observed in the rhIGF-I group was due to lower glucose values prior to breakfast, lunch, and bedtime compared to the placebo group. The glycemic profile improved throughout the treatment period in the rhIGF-I group, compared to the placebo group as shown in FIG. 14. In both groups there was some decrease in $HbA_1$ (greater than 1% in the placebo group) during the 4-week lead-in period (11.5±1.3% to 11.4±1.4%, placebo; 12.4±3.2% to 11.2±1.7%, rhIGF-I). However, during the treatment period $HbA_1$ declined further in the rhIGF-I compared to the placebo group (mean reduction of 1.8±1.25% versus 1.3±1.6%).

TABLE IV

Mean Plasma Glucose Concentrations in the Last 10 Days of Lead-in and Treatment Periods (mg/dL)
For S.I. Unit Conversion Multiply by 0.0551

| | rhIGF-I | | Placebo | |
|---|---|---|---|---|
| | (Mean ± SEM) | | | |
| Time | Lead-in | Treatment | Lead-in | Treatment |
| Pre-breakfast | 188 ± 45 | 176 ± 39 | 176 ± 39 | 191 ± 40 |
| Pre-lunch | 192 ± 60 | 142 ± 56 | 188 ± 51 | 174 ± 53 |
| Pre-dinner | 229 ± 63 | 199 ± 47 | 252 ± 68 | 228 ± 63 |
| Pre-bedtime | 206 ± 76 | 171 ± 51 | 185 ± 54 | 178 ± 42 |

Insulin usage

The use of regular and NPH insulin was evaluated separately. The insulin dose of regular and NPH insulins was standardized as units/kg/10 days. During the last ten days of the lead-in period, there were no differences between placebo and rhIGF-I groups for the average number of insulin units used daily per kg of body weight for either regular (0.27±0.10 placebo; 0.27±0.10 rhIGF-I) or NPH insulin (0.77±0.19 placebo; 0.66±0.13 rhIGF-I). In contrast, during the treatment phase, the average amount of regular insulin used in the rhIGF-I group was significantly lower (0.28±0.10 vs. 0.20±0.10; $p<0.05$). The average number of NPH units used per kg body weight was also lower during treatment for subjects receiving rhIGF-I vs. placebo (0.80±0.23 placebo; 0.65±0.14 rhIGF-I).

Hormone levels

Figure 15:
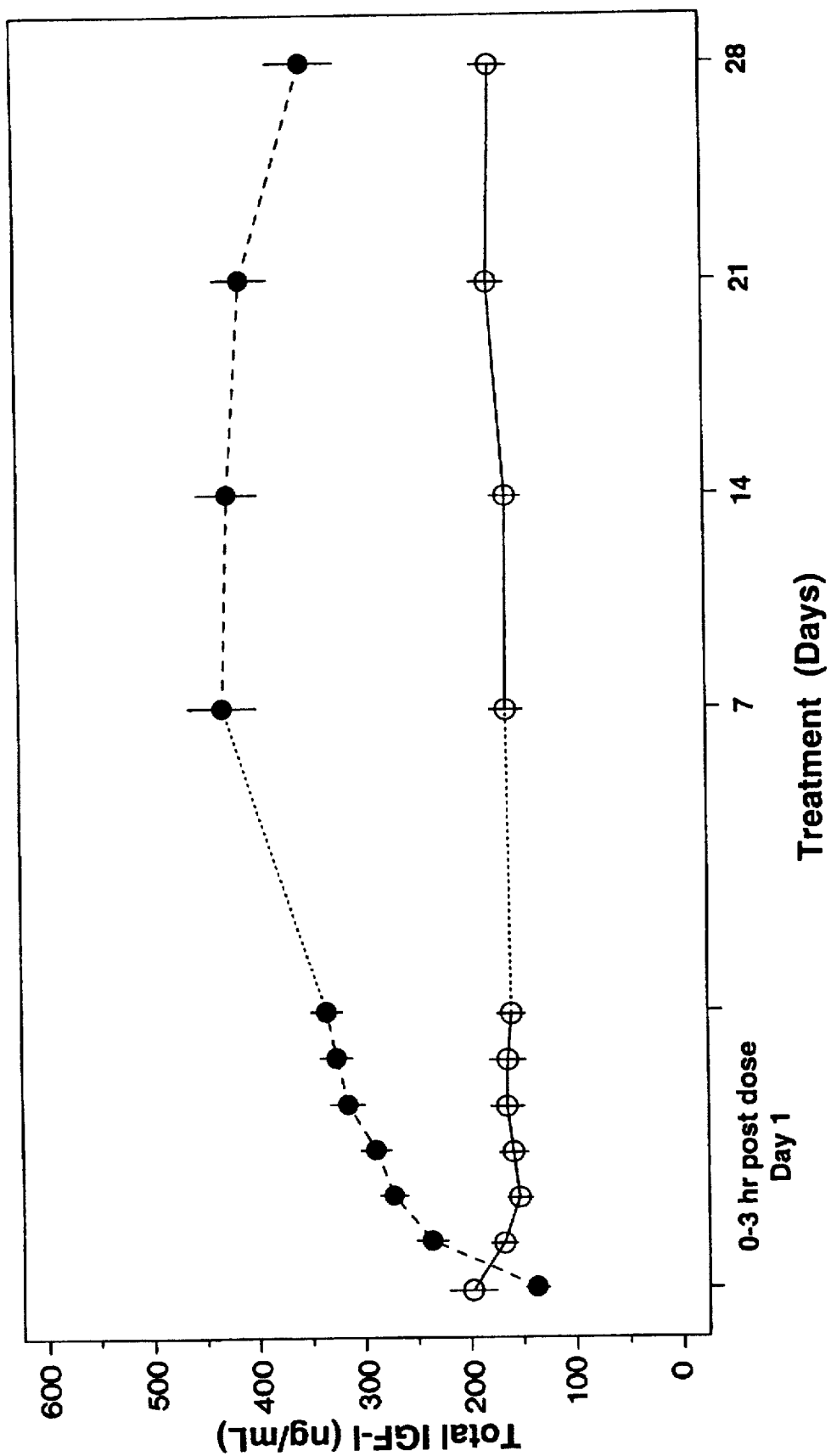
FIG. 15 shows total IGF-I levels during the treatment period for the study outlined in FIG. 13. The IGF-I levels, low in both the rhIGF-I and placebo groups during pre-treatment, were increased toward normal levels over the three hours following the first injection of rhIGF-I and remained elevated for the duration of the treatment period. The mean±SEM is illustrated.

FIG. 15 shows the total IGF-I levels during the pharmacokinetics study on day 1 of treatment and 2–4 hours following study drug administration on day 7, 14, 21, and 28 of the treatment period. Average IGF-I levels in the placebo group fluctuated between 150 and 200 ng/mL (19.6–26 nmol/L) throughout the course of the study. In the rhIGF-I group on day 1 of treatment low baseline IGF-I level (137±51 ng/mL; 17.9±6.7 nmol/L) rose to the mid-normal range (315±72 ng/mL; 41.2±9.4 nmol/L) by two hours following the first rhIGF-I injection. The IGF-I remained in the mid-normal range (340–440 ng/mL; 44–57 nmol/L) throughout the treatment period.

Figure 16:
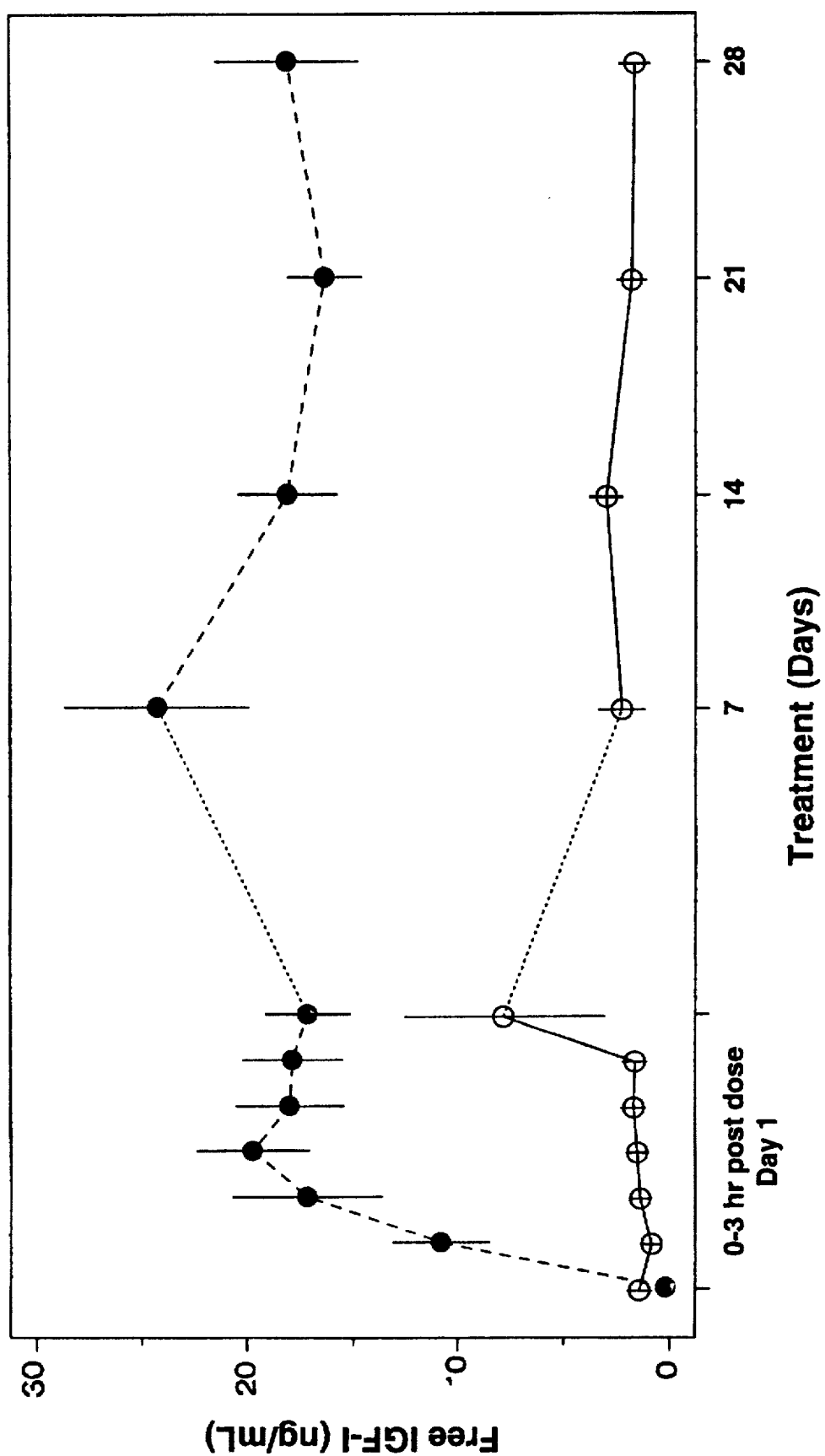
FIG. 16 shows the free IGF-I levels during the treatment period for the study outlined in FIG. 13. The free IGF-I levels, low in both the rhIGF-I and placebo groups during pre-treatment, were increased toward normal levels over the three hours following the first injection of rhIGF-I and remained elevated for the duration of the treatment period. The mean±SEM is shown.

Free IGF-I levels also rose following treatment, as shown in FIG. 16. The average free IGF-I level measured 2–4 hours after rhIGF-I injection was high on day 1 and remained elevated throughout the study. All values in the rhIGF-I-treated group were higher than those observed in the corresponding Tanner stage placebo group ($p<0.01$). The free IGF-I levels observed in the rhIGF-I group were similar to those measured in a group of healthy euthyroid controls (mean±SD), including 20 pre-pubertal controls (11.4±10.3 ng/mL) and 19 adolescents in Tanner stage 2–4 (14.5±12.3 ng/mL). Quattrin et al., "Low Plasma-Free IGF-I Levels in IDDM: Additional Evidence for a Bi-hormonal Defect in Diabetes," presentation to the 56th Scientific Sessions of the ADA—San Francisco, Calif., June 8, 18; Quattrin et al., *Diabetes*, 45 Suppl. 2: 53 (May 1996).

Safety assessments

Except for one patient who experienced a syncopal episode (described above), the only significant adverse experience reported with appreciable frequency was hypoglycemia. The median amount of hypoglycemic episodes of 2 was similar in both groups during the lead-in period. It was increased significantly in the rhIGF-I vs. placebo group during the treatment period (6 vs. 3, $p<0.05$). However, when assessed by study week, the increase in the number of hypoglycemic events was significantly higher in the rhIGF-I group only in the first week of treatment (1.6±1.4 vs 0.9±1.6, $p<0.05$). With regard to time of day, the median number of hypoglycemic episodes was significantly higher in the rhIGF-I vs. placebo group only pre-breakfast and pre-lunch throughout the entire treatment period ($p<0.05$). There was no correlation between the number of hypoglycemic events and HbA, or plasma IGF-I level on day 28 of treatment.

The biochemical, lipid, and thyroid profiles were normal at the beginning of the lead-in period and remained within normal limits throughout the duration of the study. The overall improved glycemic profile in the rhIGF-I group was not accompanied by significant increase in body weight by day 28 (from 52±13 kg to 53±13 kg in the placebo group and from 54±16 kg to 55±17 kg in the rhIGF-I group).

DISCUSSION

This example shows a placebo-controlled trial in IDDM patients demonstrating that chronic dual hormonal replacement therapy with IGF-I plus insulin is capable of safely producing better glycemic control than insulin alone. Furthermore, the improved control was achieved with significantly less insulin usage. Because prolonged improvements in glycemic control are clearly linked to improved clinical outcomes (DCCT Research Group, supra), this finding may have major implications for the future treatment of IDDM.

Because the peak IGF-I concentrations occur 2–3 hours following sc injection, the persistent acute hypoglycemic effect observed in this study suggests that rhIGF-I supplementation contributes uniquely to glucose regulation. This is further supported by the fact that, although all subjects in both groups were allowed and encouraged to use as much insulin as necessary to achieve their glucose targets, the concomitant administration of rhIGF-I resulted in better overall glycemic control associated with significantly lower insulin dose.

The only significant adverse event observed during the study in both rhIGF-I and placebo groups was hypoglycemia. The episodes were most common in the early and late morning. Importantly, there were no severe episodes and all such events resolved with oral carbohydrate administration. In the present study, a technique or design was not included to separate a true increase in hypoglycemic frequency from an enhancement in hypoglycemic awareness. It is possible that the increased number of hypoglycemic events reported could have been secondary to the increased hypoglycemia awareness following rhIGF-I administration as previously described by Kerr et al., American Diabetes Association, supra. Not observed were any of the serious adverse events previously described during intravenous rhIGF-I administration. The low drop-out rate (9.3%) and the fact that only two patients requested to discontinue the study demonstrate further the safety and low adverse effect rate during this four-week trial.

In contrast to the findings of Boulware et al., supra, no significant biochemical abnormalities were observed during the study. Also, it was not confirmed that rhIGF-I decreased triglycerides and the ratio of total cholesterol to high-density lipoprotein (HDL) cholesterol, as reported by Guler et al., *Acta Paediatr. Scand.*, 367, supra. The lipid profiles were in or near the normal range for most of the subjects prior to entering the trial (day 1 mean cholesterol 172±32 mg/kL or 4.5±0.8 mmol/L). The lipid-improving effects of rhIGF-I may be better demonstrated in patients with more substantial abnormalities before treatment or through different dose levels or regimens.

In conclusion, these results suggest that IGF-I/insulin combination therapy may provide clear and unique benefits beyond insulin therapy alone. Because this trial employed only one well tolerated dose, administered once a day in the morning, it is likely that higher doses, more frequent administration, and/or shifting the dose to the evening may result in even better glycemic control.

What is claimed is:

1. A parenteral composition comprising IGF-I and NPH insulin, in amounts of from about 1 to 10 mg IGF-I and from about 0.2 to 2 mg NPH insulin, in a parenterally acceptable carrier.

2. The composition of claim 1 that is injectable.

3. The composition of claim 2 wherein the carrier is an acetic acid salt buffer.

4. The composition of claim 1 that is sterile.

5. The composition of claim 1 additionally comprising an osmolyte and a stabilizer.

6. The composition of claim 1 additionally comprising sodium chloride, and benzyl alcohol or phenol, in an acetate buffer at pH from about 5 to 6.

7. The composition of claim 6 additionally comprising polysorbate or poloxamer in an amount of from about 1 to 3 mg/mL.

8. The composition of claim 1 additionally comprising a surfactant.

9. The composition of claim 1 wherein the weight ratio of NPH insulin to IGF-I in the composition ranges from about 10:1 to 1:50.

10. The composition of claim 1 wherein the IGF-I is human IGF-I and the NPH insulin is human NPH insulin.

11. A composition comprising IGF-I and NPH insulin in an acetic acid salt buffer at a pH of about 4.5 to 8.

12. The composition of claim 11 that is parenteral and sterile.

13. A composition comprising IGF-I and NPH insulin in a weight ratio of NPH insulin to IGF-I of from about 10:1 to 1:50 (w/w), from about 0.05 to 0.3M of an osmolyte, from about 0.1 to 10 mg/mL of a stabilizer, and from about 5 to 100 mM of an acetic acid salt buffer at from about pH 5 to 7.

14. The composition of claim 13 that is parenteral and sterile.

15. The composition of claim 13 additionally comprising from about 1 to 5 mg/mL of a surfactant.

16. The composition of claim 15 wherein the osmolyte is an inorganic salt and the surfactant is non-ionic.

17. The composition of claim 16 wherein the inorganic salt is sodium chloride or potassium chloride, the stabilizer is phenol or benzyl alcohol, the surfactant is polysorbate or poloxamer, the buffer is sodium acetate or sodium phosphate or both, and the amounts of IGF-I and NPH insulin are from about 1 to 10 mg and from about 0.2 to 2 mg, respectively.

18. The composition of claim 17 wherein the weight ratio of NPH insulin to IGF-I is from about 1:1 to 1:3, the amount of sodium chloride is from about 5 to 7 mg/mL, the amount of phenol is from about 0.1 to 3 mg/mL and the amount of benzyl alcohol is from about 6 to 10 mg/mL, the surfactant is polysorbate in an amount of from about 1 to 3 mg/mL, the amount of sodium acetate is from about 2.5 to 4 mg/mL, and the amount of sodium phosphate is from about 0.1 to 1 mg/mL.

19. A method for preparing the composition of claim 1 comprising mixing NPH insulin with an IGF-I formulation comprising from about 2 to 20 mg/mL of IGF-I, from about 2 to 50 mg/mL of sodium chloride, from about 1 to 15 mg/mL of a stabilizer, and a buffer at a pH of from about 5 to 5.5.

20. The method of claim 19 wherein the buffer is an acetic acid salt buffer.

21. The method of claim 19 wherein the IGF-I formulation comprises from about 8 to 12 mg/mL of IGF-I, from about 5 to 6 mg/mL of sodium chloride, a stabilizer consisting of from about 8 to 10 mg/mL of benzyl alcohol or from about 2 to 3 mg/mL of phenol, or both from about 8 to 10 mg/mL of benzyl alcohol and from about 2 to 3 mg/mL of phenol, and an about 50 mM sodium acetate buffered solution at a pH of about 5.4 and the NPH insulin is at a concentration of about 4 mg/mL.

22. The method of claim 19 wherein the mixing takes place in a syringe.

23. A composition comprising NPH insulin in an acetic acid salt buffer without the presence of IGF-I.

24. The composition of claim 23 that is parenteral and sterile.

25. The composition of claim 23 additionally comprising from about 2 to 50 mg/mL of sodium chloride and from about 1 to 15 mg/mL of a stabilizer, at a pH of from about 5 to 5.5.

26. The composition of claim 23 additionally comprising from about 5 to 6 mg/mL of sodium chloride, a stabilizer consisting of from about 8 to 10 mg/mL of benzyl alcohol or from about 2 to 3 mg/mL of phenol, or both from about 8 to 10 mg/mL of benzyl alcohol and from about 2 to 3 mg/mL of phenol, and the buffer is an about 50 mM sodium acetate buffered solution at a pH of about 5.4.

27. A method for treating a hyperglycemic disorder in a mammal comprising administering to the mammal an effective amount of the composition of claim 1.

28. The method of claim 27 wherein the administration is subcutaneous.

29. The method of claim 27 wherein the administration is by injection.

30. The method of claim 29 wherein the number of daily injections of the composition is reduced over the number of daily injections when insulin without IGF-I is administered to the mammal.

31. The method of claim 27 wherein the hyperglycemic disorder is diabetes.

32. The method of claim 27 wherein the mammal is human.

33. The method of claim 27 additionally comprising administering to the mammal an effective amount of a hypoglycemic agent.

34. The method of claim 27 wherein an effective amount of an IGF binding protein or acid-labile subunit or both is administered together with the IGF-I and NPH insulin.

35. The method of claim 27 wherein the IGF-I is complexed with an IGF binding protein or acid-labile subunit or both.

36. A method for treating a hyperglycemic disorder in a mammal comprising administering to the mammal an effective amount of the composition of claim 11.

37. A method for treating a hyperglycemic disorder in a mammal comprising administering to the mammal an effective amount of the composition of claim 13.

38. A method for treating a hyperglycemic disorder in a mammal comprising administering to the mammal an effective amount of the composition of claim 23.

39. A kit comprising:

(a) a container comprising IGF-I in a pharmaceutically acceptable acetic acid salt buffer at a pH of about 4.5 to 8;

(b) a container comprising pharmaceutically acceptable NPH insulin; and (c) instructions for combining the contents of containers (a) and (b) to provide a pharmaceutically acceptable formulation.

40. The kit of claim 39 wherein the pharmaceutically acceptable formulation is for treating diabetes.

41. The kit of claim 39 wherein container (a) additionally comprises sodium chloride and benzyl alcohol or phenol, or both, in the buffer at a pH of from about 5.0 to 5.5.

42. The kit of claim 41 wherein container (a) comprises from about 8 to 12 mg/mL of IGF-I, from about 5 to 6 mg/mL of sodium chloride, from about 8 to 10 mg/mL of benzyl alcohol or from about 2 to 3 mg/mL of phenol, or both from about 8 to 10 mg/mL of benzyl alcohol and from about 2 to 3 mg/mL of phenol, in an about 50 mM sodium acetate buffered solution at a pH of about 5.4.

43. The kit of claim 42 wherein container (a) additionally comprises from about 1 to 3 mg/mL polysorbate.

44. The kit of claim 39 wherein the containers are vials and the instructions specify combining the contents of containers (a) and (b) in a syringe for immediate injection.

45. The composition of claim 11 wherein the pH of the buffer is from about 5 to 7.

46. A composition comprising NPH insulin in an acetic acid salt buffer at a pH of about 4.5 to 8.

47. The composition of claim 23 wherein the pH of the buffer is from about 4.5 to 8.

48. The composition of claim 39 wherein the pH of the buffer is from about 5 to 7.

* * * * *